(12) United States Patent
Durrer et al.

(10) Patent No.: US 10,744,168 B2
(45) Date of Patent: Aug. 18, 2020

(54) GENETICALLY MODIFIED PROBIOTIC FOR THE TREATMENT OF PHENYLKETONURIA (PKU) DISEASE

(71) Applicant: University of North Texas, Denton, TX (US)

(72) Inventors: Katherine Durrer, Irving, TX (US); Michael Allen, Denton, TX (US); Ione Hunt von Herbing, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 329 days.

(21) Appl. No.: 15/800,529

(22) Filed: Nov. 1, 2017

(65) Prior Publication Data

US 2018/0117101 A1  May 3, 2018

Related U.S. Application Data

(63) Continuation-in-part of application No. 14/417,176, filed as application No. PCT/US2013/052200 on Jul. 26, 2013, now abandoned.

(60) Provisional application No. 61/676,461, filed on Jul. 27, 2012.

(51) Int. Cl.
| | | |
|---|---|---|
| A61K 35/747 | (2015.01) | |
| A61K 38/51 | (2006.01) | |
| A61K 9/00 | (2006.01) | |
| A61P 3/00 | (2006.01) | |

(52) U.S. Cl.
CPC .......... *A61K 35/747* (2013.01); *A61K 9/0053* (2013.01); *A61K 38/51* (2013.01); *A61P 3/00* (2018.01); *C12Y 403/01024* (2013.01)

(58) Field of Classification Search
CPC .......... C12Y 403/01024; A61K 35/747; A61K 9/0053; A61K 38/51; A61P 3/00
See application file for complete search history.

(56) References Cited

U.S. PATENT DOCUMENTS

2009/0038023 A1* 2/2009 Weiner et al. ............... 800/13

* cited by examiner

*Primary Examiner* — Satyendra K Singh
(74) *Attorney, Agent, or Firm* — Jackson Walker LLP

(57) ABSTRACT

A GMP adapted to provide the PAL gene for the treatment of PKU when administered orally. The GMP of the present invention may include a probiotic, a PAL gene to be expressed using the probiotic, wherein the PAL gene is functionally attached to a promoter and a ribosome binding site, and may be codon-optimized for expression in a certain host organism. A method of treating the metabolic disease of PKU by oral administration and ingestion of a GMP is also provided.

7 Claims, 5 Drawing Sheets

Specification includes a Sequence Listing.

GENETICALLY MODIFIED PROBIOTIC FOR THE TREATMENT OF PHENYLKETONURIA (PKU) DISEASE

This application is a continuation-in-part of U.S. patent application Ser. No. 14/417,176, filed on Jan. 26, 2015, entitled "Genetically Modified Probiotic For the Treatment of Phenylketonuria (PKU) Disease," which is hereby incorporated by reference for all purposes as is set forth herein in its entirety.

BACKGROUND

The present invention relates to a genetically modified probiotic (GMP), and more specifically to a GMP adapted to provide the phenylalanine ammonia-lyase (PAL) gene or other phenylalanine-degrading enzyme for the treatment of phenylketonuria (PKU). The GMP is herein referred to as PHEnominal.

Advantages Over Conventional Technologies

PKU is a disease that renders the patient incapable of digesting the amino acid phenylalanine, resulting in a subsequent accumulation in the blood causing toxicity.

Several technologies have been developed for the treatment of PKU. First, liver and/or hepatocyte transplants have been used. A regular transplant is not considered an acceptable treatment by insurance companies as the cost of treatment for PKU transfers to the cost of treatment to prevent organ rejection.

Second, gene therapy techniques have been utilized for the treatment of PKU. Gene therapy methods have yet to break the barrier of gene silencing. In gene silencing, a eukaryotic cell detects genes of a viral source, such as a gene therapy vector, and methylates the DNA to silence it. Additionally, after the "Bubble boy" syndrome incident (children developing leukemia following gene therapy for a terminal illness), gene therapy has not gained wide spread acceptance or regulatory approval in the USA.

Finally, several other treatments have been tried, without the level of cost-effectiveness required for wide-spread adoption.

Other treatments for PKU patients are made difficult by the many co-factors and co-enzymes required for PAH (the deficient enzyme) to function. Current dietary therapies cost approximately $40,000.00 per year for a teen or adult. Co-factor therapy, which supplies an excess of PAH's co-factor, reduces phenylalanine (phe) in some of the patients. However many patients (40-50%) see no improvements, or improvement is not sufficient to warrant the cost of co-factor therapy. The cofactor therapy by the name of Kuvan®, is also very expensive ($100,000.00 per year for an adult or teen). Responses from this treatment range from no change to complete control of phenylalanine levels. It is thought that the patient's level of response to this therapy is dictated by the exact genetic mutation they carry.

PEG-PAL, is currently under clinical trials. For this treatment, PAL is produced by bacteria, purified, and coated in polyethylene glycol (PEG). The resulting PEG-PAL is injected subcutaneously into the patient, and enters the blood stream. Once in the blood, the PEG coating helps protect PAL from immunodetection while allowing the enzyme to degrade serum phenylalanine. Although cost estimates have not been released, similar therapies (PEG-Adenosine deaminase) are quite expensive. Additionally, complications of this therapy have been detected in phase 2 clinical trials.

Yeast PAL in microcapsules has also been studied as a potential treatment. This study used rats injected with phenylalanine rather than a true disease model. Yeast PAL has lower activity (cannot compare exactly, due to notation used), and of further concern, yeast PAL is nearly as good at catabolizing tyrosine as phe (0.67 micromoles/min per unit enzyme for tyrosine and 1.4 micromoles/min per unit enzyme at catabolizing phe). The latter is of particular concern since PKU patients also are unable to synthesize the essential amino acid tyrosine from phe. Additionally, microcapsules were deemed too expensive to use as a PKU therapy.

Oral naked PAL enzyme has been developed, but was only used in mice due to the restrictions of treatment. Namely, the PAL enzyme could not survive the stomach to arrive in the intestine unless it was given by gastric gavage along with enough sodium bicarbonate to neutralize the stomach acid. Furthermore, once in the intestine, PAL is cleaved rapidly by proteases such as trypsin and chymotrypsin.

The only current option known to work as a treatment in all patients with PKU is dietary restriction of the ingestion of foods containing phe. No natural protein is free of phe, and only a handful of proteins have been identified as having low phe contents. To this end, restricting phe ingestion can be fostered by the ingestion of synthetic foods. These foods are reported as having repugnant odor and flavor, resulting in poor dietary compliance. In addition to a diet more limited than that of a person with gluten intolerance, and the cost of the synthetic food diet is similar to that of the co-factor therapy ($1,000.00 per month for infant formula, with costs increasing as the patient becomes an adult and requires more food). Insurance companies commonly deny assistance with the food expenses of this treatment.

The invention described herein meets the need for a cost-effective therapy for PKU, with tolerable side-effects and high efficacy.

SUMMARY

The present invention relates to a GMP adapted to provide the PAL gene or other phenylalanine-degrading enzyme for the treatment of PKU. In certain embodiments, the GMP of the present invention comprises a probiotic, a PAL gene to be expressed using the probiotic, wherein the PAL gene is functionally attached to a promoter and a ribosome binding site, and may be codon-optimized for expression in a certain host organism.

The present invention further comprises a method of treating the metabolic disease of PKU by oral administration and ingestion of a GMP. The GMP described herein will produce the enzyme PAL in the intestine when administered orally. The genetically engineered PAL will digest ingested phenylalanine contained in most proteinous foods. The end result will be that phenylalanine obtained from ingestion is not absorbed into the blood stream and cannot build up to toxic levels.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1A:
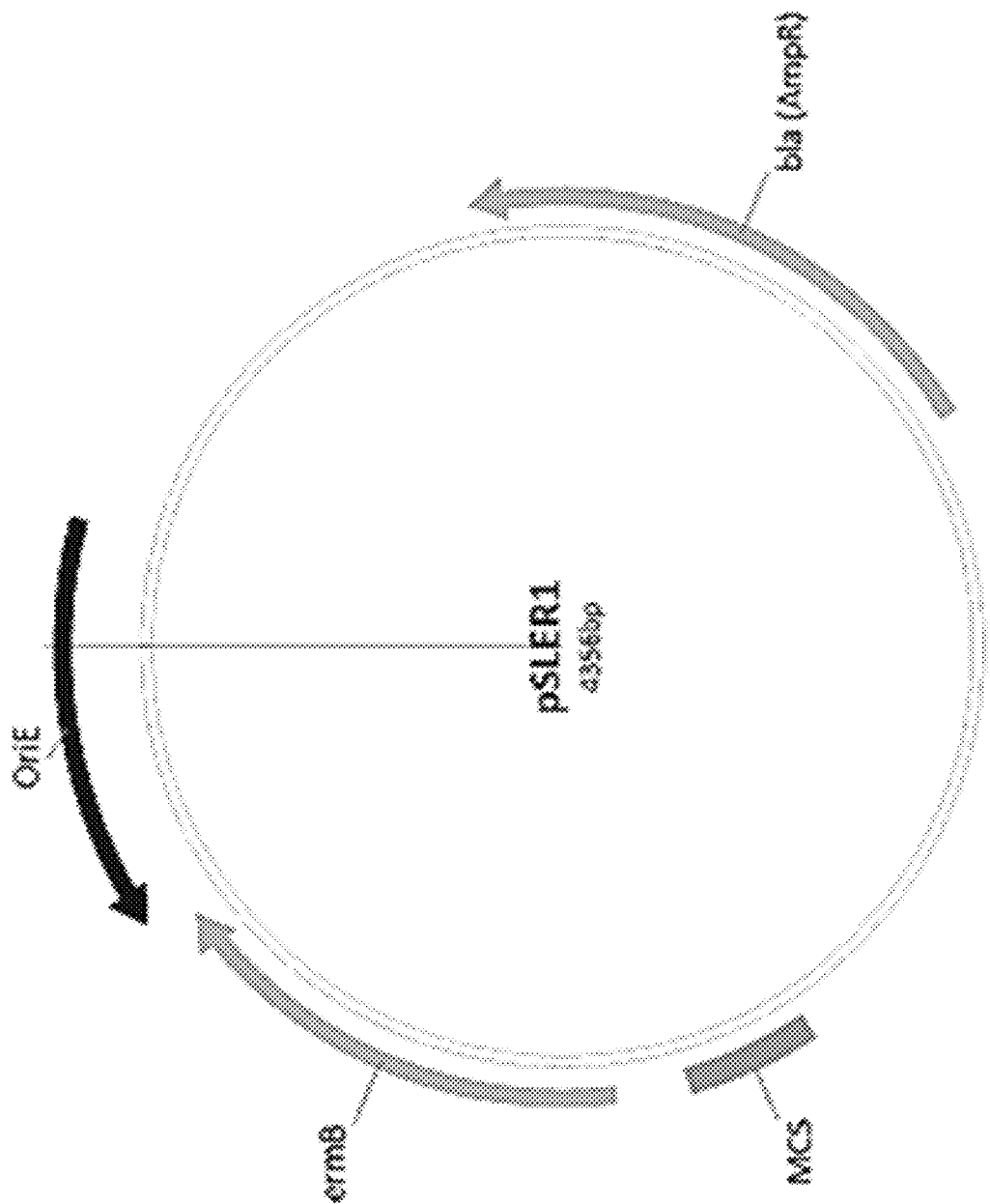
FIG. 1A shows a step in the creation of the final functional mouse therapy shuttle vector, starting with the *E. coli* plasmid pSLER1.

One aspect of the present invention pertains to a genetically modified probiotic (GMP) to deliver functional PAL enzyme or other phenylalanine-degrading enzyme to the body of an animal, preferably to the small intestine. In certain embodiments, the probiotic is/has 1) capable of surviving the acid of the stomach and maintaining functionality after exiting the stomach; 2) capable of maintaining functionality and metabolic activity in the small intestine, and expressing the PAL gene or other phenylalanine-degrading enzyme in the intestine; 3) a mouse trophic and human trophic strain; 4) safe for oral use as a human probiotic; 5) capable of being produced in-vitro; and 6) amendable to electropration or another form of transformation.

In some embodiments, the probiotic capable of delivering functional phenylalanine-degrading enzyme, such as PAL enzyme, is useful in the treatment of PKU. If phenylalanine is pulled from the intestinal lumen by probiotics to be degraded by bacterial cells, phe will not enter the blood and will be unable to cause its pathogenic effects in a PKU animal/patient.

In certain embodiments, the probiotic is any of the genera of probiotic bacteria. Examples of probiotics include, but are not limited to, the *Lactobacilli* and *Lactococci* genera, which are used in yogurts and probiotic supplements in the USA, and would serve well as a safe delivery system to treat disease. Strain specificity may be selected based on the organism in which the treatment is occurring (i.e. a mouse specific strain may be selected for mouse in-vivo experimentation, while a human specific strain may be selected for human clinical trials and human treatment).

Because amino acid absorption occurs in the small intestine, a probiotic may be selected that is metabolically active in, and preferentially lives in the small intestine. Strains of *Lactobacillus reuteri* exist for mouse and human, and the microbe adheres to mucus of small intestine in both cases. Finally, a high in vivo retention rate of foreign DNA in this organism can be achieved by using a specific plasmid section in the final shuttle vector. Integration of the desired gene into the chromosome may also be performed if desired.

Additional probiotics other than *Lactobacillus reuteri* may be used as well, including various different probiotics from the *Lactobacilli* and *Lactococci* genera. The same promoters and genes that function in one species of *Lactobacillus* will function in other species of *Lactobacillus*. For example, the ldh promoter from *Lactobacillus acidophilus* works in *Lactobacillus reuteri*, and the ermB promoter works in multiple *Lactobacillus* strains. There is also common relevant codon usage across different species in the *Lactobacillus* genus. For example, five species of *Lactobacilli*—*L. acidophilus, L. brevis, L. casei, L. plantarum*, and *L. reuteri*—all preferentially use the AGA codon for Arginine and use the AGG Arginine codon rarely. Similarly, the codon of ATA for Isoleucine is rarely used while the other two codons of ATT and ATC have much higher usage frequencies. Thus, a gene codon optimized for one *Lactobacillus* species works quite well in any other *Lactobacillus* species, and primers and genes that function in one *Lactobacillus* species will function in other *Lactobacillus* species as well. In one preferred embodiment described herein, the gene construct FuzErmAvPAL used on a plasmid in *L. reuteri* was inserted into the chromosome of *L. acidophilus* with no additional changes or adjustments to the gene itself. The probiotic *L. acidophilus* bacterium functioned effectively, just as the *L. reuteri* bacterium did.

The enzyme for phenylalanine (phe) degradation may be selected from the enzyme family of Phenylalanine Ammonia Lysases (PALs). PAL enzymes cleave phenylalanine into trans-cinnamic acid and ammonia, both of which are safely and readily cleared from the mammalian body. Unlike other phe catabolizing enzymes, PAL enzymes do not require co-factors or co-enzymes to fuction. Optimal pH ranges for PAL enzymes are also compatible with physiological pH of the intestine. The multiple potential sources of PAL include plants such as parsley (*Petroselinum crispum*), eubacteria (*Streptomyces maritimus*), cyanobacteria (*Anabaena variabilis, Nostoc punctiforme*) and yeast (*Rhodoturula glutinis*) or other as yet un-discovered sources.

The selected PAL gene may be codon optimized to allow for successful synthesis (translation) of the enzyme in its probiotic host. This is because each organism has a different codon usage frequency for translating mRNAs into proteins/enzymes, and the PAL gene to be inserted must comply with the host codon usage rather than that of its donor. Each organism typically has multiple codon choices available for each amino acid (AA). Therefore, there are multiple potential DNA sequences that may be used in any particular organism that will result in the same AA sequence while still complying with the probiotic host's codon usage.

Modifications in front of the gene selected for the GMP system may be generated to regulate transcription, translation, and location of the translated PAL enzyme. Additionally, a transcriptional terminator may be added to the end of the gene. Restriction sites may be added as needed throughout the gene. In general, known protocols will be used for DNA amplification, electrophoresis and isolation. In some cases, gel electrophoresis may be conducted in an agarose gel loaded in a "mirror" pattern, such that the same samples are loaded in wells equidistant from an imaginary line running down the center of the gel. After running the gel, the gel will be cut in half along the center of the "mirror". One half will be stained with Ethidium bromide and visualized. The visualized bands will be measured for distance from the load point, and that measurement will be used to cut out the band on the unstained (Ethidium bromide free) half of the gel. This reduces the likelihood of spontaneous mutation during handling.

Transcription: A promoter with constitutive expression may be selected and placed in front of the PAL gene in order to drive transcription of the gene. The promoter may be active in vivo, or both in vivo and in vitro. Several examples of good constitutive promoters in *Lactobacilli* and *Lactococci* include, but are not limited to: ermB, ldhL, lacA, and slp. It is also possible to place a promoterless PAL gene in tandem behind a gene with a functional promoter as long as the gene with a functional promoter does not contain an intervening termination sequence. If the gene with a promoter does contain a termination sequence, the PAL gene must disrupt the original termination sequence while replicating the termination sequence at the end of PAL.

Translation: Following the promoter there may be a ribosome binding site (RBS) with an appropriate length of spacer prior to the start codon. Although there are some general similarities of RBS sequences and spacer length amongst prokaryotes, each species has its own preferences. For *Lactobacillus* and *Lactococci*, a RBS that is rich in adenine (A) and guanine (G) and is 5-6 bases in length appears to be optimal. The spacer following the RBS and ending at the start codon tends to be between 7 and 13 bases long.

Enzyme location: If it becomes desirable to secrete PAL to the cell's exterior, a secretion tag from another enzyme may be added. Examples include, but are not limited to, the secretion tags from the genes Lp_0373, amyL, nip1, usp45, and snub.

The final gene construct for the GMP system must be introduced into the probiotic in a stable manner. This may be done by any suitable technology, such as by placing a PAL gene construct into an existing high retention plasmid or high retention shuttle plasmid (with or without a selection cassette), synthetically creating a high retention plasmid/shuttle plasmid, homologously recombining the PAL gene into the probiotic's chromosome, phage transduction, or usage of a transposable element. A high retention plasmid is designed to be retained in the bacteria for several generations in the absence of selective pressure. If selection is used in the mouse version of this treatment, an antibiotic resistance gene may be used, such as an ampicillin or erythromycin resistance gene. In some embodiments, erythromycin resistance genes C, B, or GT may be used. An *E. coli* origin of replication to the plasmid may be used, such as the origin in pUC19 (originally from pMB1). In a human version of this treatment, and FDA approved selection cassette would be used, as antibiotic resistance is not acceptable in human probiotics.

After transformation of the probiotic with the gene construct, in vitro phe metabolism by the GMP can be assessed by testing for an increase in absorbance at a wavelength of 280 nm indicating increase in trans-cinnamic acid production.

The genetically modified probiotic "PHEnominal" organism disclosed herein will have the ability to live in the small intestine, where it will break down phenylalanine (phe) prior to its absorption into the blood stream. By preventing excess phenylalanine from entering the blood stream, phenylalanine toxicity will be prevented.

In certain embodiments, the probiotic organism of the present invention will be delivered to an animal or patient as a purified microbe free of any culture media. Purified probioitic organisms may be administered in a pill, powder or drops. These methods of administration have the advantage that a higher quantity of the organism may be delivered than with a culture medium such as yogurt (i.e. the potential quantity of yogurt to be ingested could be much more than would typically be consumed). Moreover, a purified probiotic organism such as the present invention does not present problems with lactose or dairy intolerant patients, or infants who are not ready to eat solid foods. Finally, administration by pill, powder or drops has the advantage that the probiotic organism can be administered with a range of foods, and patients will not develop a dislike of a food eaten every day, as could be the case with probiotic delivered in yogurt.

The appropriate dosage of the GMP system can be calculated by measuring the number of live organisms which must be consumed by an animal to be recovered live from the feces. This number can be combined with survival tests of the probiotic to arrive at an approximate dosage.

The genetically engineered probiotic can be tested as a treatment using an animal model, for example the PAHenu2 mouse on the C57BL6 background with the appropriate controls. Blood collection can be used to assess serum phe throughout the experiment. Tissue collection at the end of experiment will allow for other health assessments.

Shipping costs of the probiotic organism of the present invention in a purified and freeze-dried form will be more cost-effective than shipping of probiotic in a culture medium, such as yogurt, which may need to be refrigerated, and which may weigh significantly more. Moreover, the administration of purified probiotic in pill, powder, or drop form, as in the present invention, may allow a greater deree of dosage tailoring from patient to patient and possibly day to day for the same patient than probiotic delivered in culture media such as yogurt.

Patients with PKU have typically not eaten dairy products due to their high phe content. The sudden addition of regular and potentially high amounts of dairy could cause side effects in these patients, which would again favor the administration of purified microbe in pill, powder or drop form, as described herein.

Probiotics are comparatively inexpensive to produce. Because the proposed genetically modified probiotic would be classified as a "drug", it may be more likely to be accepted by insurance companies as a treatment they cover (when compared to synthetic foods). Using a phenylalanine degrading probiotic will likely result in higher treatment compliance, as it will allow patients to maintain a more normal diet and life style and not one in which they would have to ingest distasteful foods. As treatment with "PHEnominal" would require oral administration, it would not require injections as with the PEG-PAL treatment (see above).

EXAMPLE 1

Construction of a GMP System—PHEnominal

The species *Lactobacillus reuteri* is used as the probiotic. Strains of this organism are found in the small intestine of most higher animals including humans and mice. Strains that are human and mouse specific have been identified and studied. For the proof of principal experiments in-vitro and the mouse in-vivo work, we will use *Lactobacillus reuteri* 100-23C. This strain has no indigenous plasmids and is capable of colonizing the small intestine of *Lactobacillus* free mice. When progressing to human clinical trials, a human specific strain of *L. reuteri* or an alternative probiotic as approved by the FDA will be used.

Figure 1B:
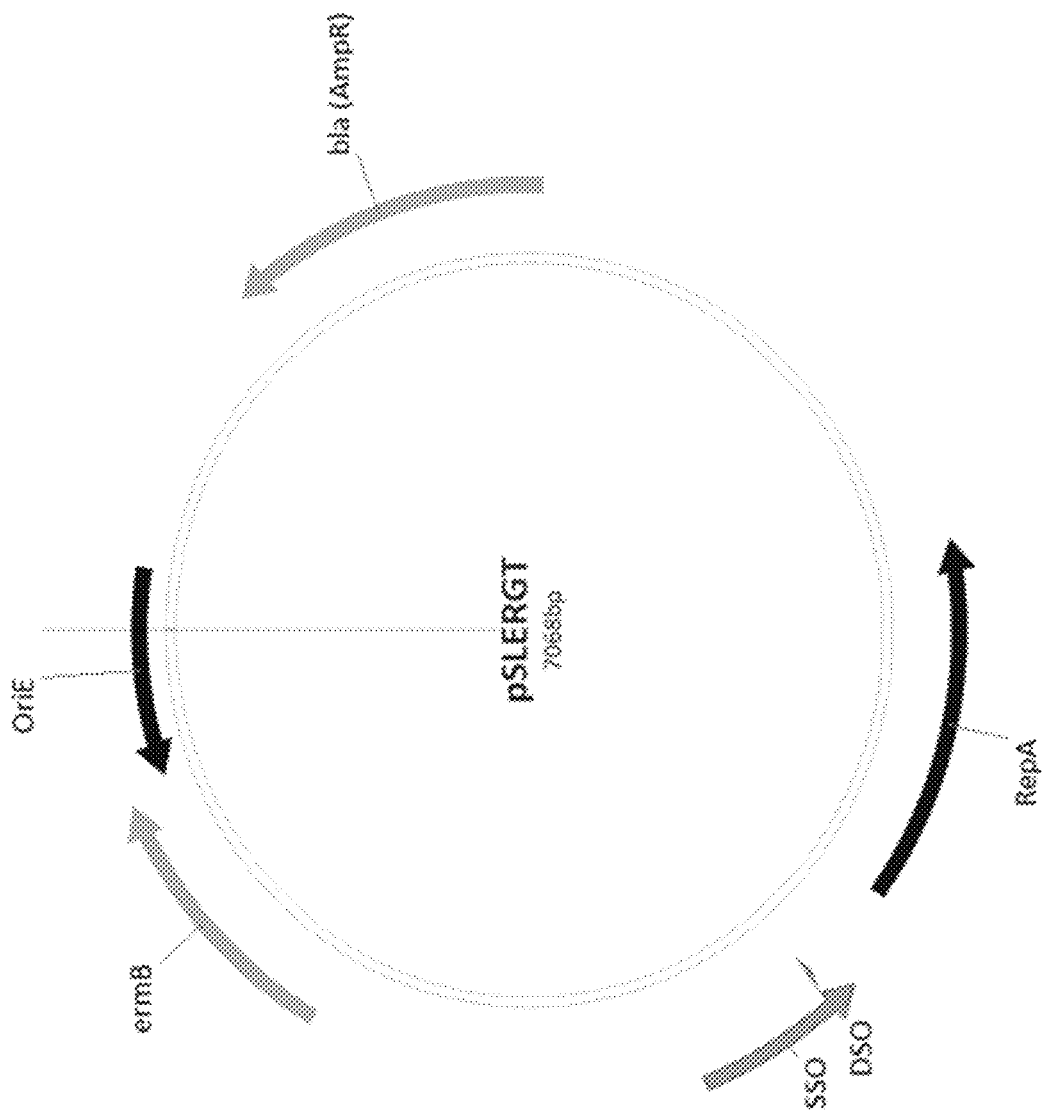
FIG. 1B shows a step in the creation of the final functional mouse therapy shuttle vector, with the addition of the pGT232 fragment to create shuttle vector ability.
Figure 1C:
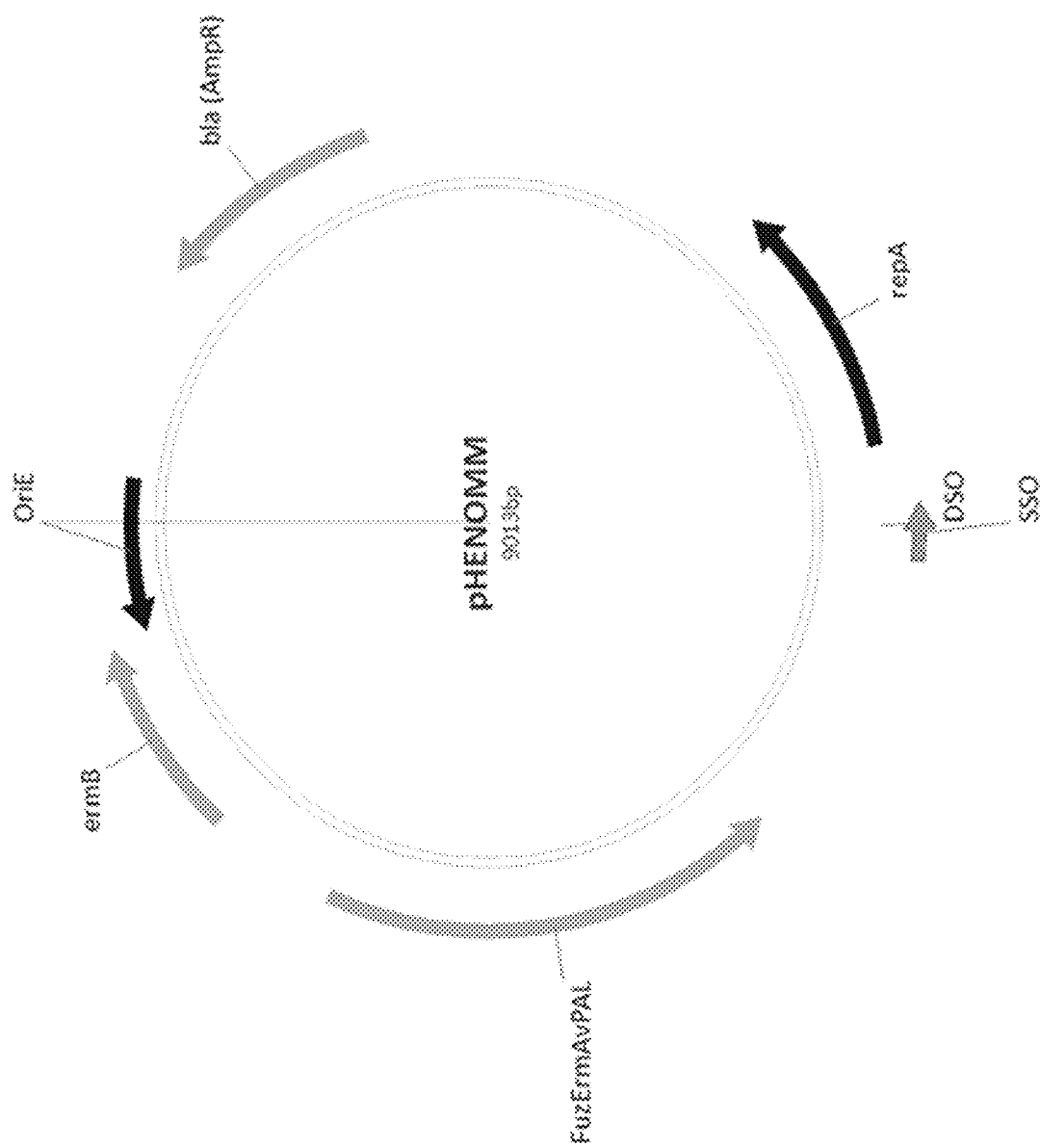
FIG. 1C shows a step in the creation of the final functional mouse therapy shuttle vector, with the final addition of FuzErmAvPAL for AvPAL expression when in a probiotic host.

The PAL enzyme to be used is from the cyanobacterium *Anabaena variabilis* ATCC 29413, referred to hereinafter as AvPAL. The sequence for this gene will be codon optimized to match codon usage for the *Lactobacillus reuteri* species as a whole. The codon optimization matches codon usage for related species as well, including *Lactobacilli* as a whole. The AvPAL front sequence (SEQ ID NO: 1) will be placed in front of the codon optimized gene to act as an RBS and spacer sequence. At the end of the gene, the AvPAL end sequence (SEQ ID NO: 2) will be added to act as a transcriptional terminator. This promoterless AvPAL construct (AvPAL plus the above detailed additional sequences) will be synthesized (BioBasic Inc., Ontario, Canada). The complete AvPAL is shown in SEQ ID NO: 3. All sequences not otherwise noted are right facing and in the standard left to right orientation. Plasmids pSLER1, pSLERGT, pHE-NOMM, and pHENOMM-sec are all left facing and are read right to left. In all plasmids it should be noted that the ermB gene is in the opposite orientation of the plasmid, and this gene is right facing reading left to right (as depicted by plasmid maps in FIGS. 1A, 1B, and 1C).

A promoter is attached to the AvPAL construct in order to create a functional AvPAL construct. The ermB promoter region with 10 additional bases inserted (SEQ ID NO: 4) was selected. This process of fusing the synthesized synthetic ermB promoter to AvPAL created the final gene product of FuzErmAvPAL (SEQ ID NO:15) and was performed by BioBasic Inc, Ontario, Canada. Additionally, the secretion tag of Lp_0373 (SEQ ID NO: 5) may be inserted between the ermB promoter and the start codon of the AvPAL gene for secFuzErmAvPAL (SEQ ID NO:6). Once the full construct was created, BioBasic ligated FuzErmAvPAL and secFuzErmAvPAL separately into our synthetically created shuttle vector pSLERGT.

Once FuzErmAvPAL and secFuzErmAvPAL have been synthesised, they must become part of a functional *Lactobacillus reuteri* shuttle plasmid. The shuttle plasmid to be used, pSLERGT (SEQ ID NO: 7), was created specifically for the mouse project by using an antibiotic resistance gene such as erythromycin resistance genes C, B, or GT as the selection cassette, the pGT232 fragment from pNCKH103 (SEQ ID NO: 8) for stability in vitro and in vivo in a *Lactobacillus reuteri* host even in the absence of selection, and *E. coli* origin of replication for shuttle function. The *E. coli* vector pSLER1 (SEQ ID NO: 9) contains the elements ermB (erythromycin resistance gene B) and *E. coli* origin of replication and will be used as the back bone of shuttle vector creation because of these properties. For a human safe plasmid, a selectable gene such as heavy metal resistance or alanine racemase (for complementation) may be used instead of antibiotic resistance. It is also possible in mouse or human safe version to integrate the desired functional AvPAL construct directly into the chromosomal DNA.

To create the desired shuttle vector of pSLERGT, plasmid DNA of pNCKH103 was harvested from 100-23 cells to allow extension PCR of the pGT232 fragment. The reaction used a forward primer for pGT232 amplification (SEQ ID NO: 10) and a reverse primer for pGT232 amplification (SEQ ID NO: 11). The following reaction mixture of New England Biolabs Q5 High Fidelity DNA polymerase was used for a 30 µl volume per reaction tube.

| | |
|---|---|
| 10x Q5 polymerase reaction Buffer | 6 µl |
| pNCKH103 DNA from L. r. 100-23 | 1.5 µl of 15 ng/µl total DNA* |
| Forward Primer | 1.5 µl |
| Reverse Primer | 1.5 µl |
| dNTP 10 mM | 2.4 µl |
| Water | 18.6 µl |
| Q5 DNA polymerase | 0.25 µl |

*Total DNA, rather than plasmid DNA, is reported due to the dirty quality of DNA extracted from L.r.100-23 cells.

The thermocycler conditions used for amplification were

| Step | ° C. | Time (minutes:seconds) |
|---|---|---|
| 1 | 98.0 | 0:30 |
| 2 | 98.0 | 0:10 |
| 3 | 57.0 | 0:12 |
| 4 | 72.0 | 1:30 |
| 5 | go to step 2, x4 | |
| 6 | 98.0 | 0:10 |
| 7 | 65.0 | 0:12 |
| 8 | 72.0 | 1:30 |
| 9 | Go to step 6, x29 | |
| 10 | 72 | 2:00 |
| 11 | 4 | ∞ |

The resulting PCR products were then run on a 0.8% agarose gel with 0.5% TBE. Gels run to optimize the reaction conditions were run with ethidium bromide incorporated into the gel. Gels for harvesting DNA for plasmid creation were run in the absence of Ethidium Bromide. For harvesting, the gel was loaded such that the first lane was a DNA ladder, and as many remaining lanes as could be filled contained PCR product. Once the Coomassie blue band reached the end of the gel, electrophoresis was stopped. The gel was cut into 2 sections, so that lanes 1 and 2 were together and the remaining lanes in the second portion. The gel segment with lanes 1 and 2 was stained in a 0.5% TBE ethidium bromide bath in a rocker for 20 minutes to visualize the PCR products with a Fotodyne Incorporated Imager and Foto/Analist PC Image software. The desired pGT232 fragment was excised from this stained portion, and revisualized to confirm appropriate cutting. This stained gel was then used as a guide to cut the appropriate bands from the lanes in the unstained portion of the gel. The bands that were never exposed to ethidium bromide or UV light were used in the UltraClean® GelSpin® DNA Extraction Kit (MoBio Laboratories, Inc., Carlsbad, Calif.). DNA post gel purification was quantitated with a Nanodrop photo spectrometer.

The PCR created pGT232 fragment was cut using NcoI FastDigest (Thermoscientific) for one sticky and one blunt end. The *E. coli* vector/backbone for insertion of the PCR product, pSLER1, was cut using FastDigest enzymes NcoI and SmaI resulting in a sticky blunt vector. Reactants for the reactions as follows

| pGT232fragment digest |
|---|
| 4 µl of pGT232fragment at 17 ng/µl |
| 0.5 µl 10x ThermoScientific FastDigest buffer |
| 0.5 µl Thermoscientific FastDigest NcoI enzyme |

| pSLER1 digest |
|---|
| 1.3 µl pSLER1 at 750 ng/µl |
| 14.7 µl water |
| 2 µl 10x ThermoScientific FastDigest buffer |
| 1 µl Thermoscientific FastDigest NcoI enzyme |
| 1 µl Thermoscientific FastDigest SmaI enzyme |

The reactions were incubated in a 37° C. water bath for 1.5 hours.

Small DNA fragments created by the digests and the enzymes used were removed from the desired DNA using the solutions protocol of the UltraClean® GelSpin® DNA Extraction Kit (MoBio Laboratories, Inc., Carlsbad, Calif.)

and eluted into molecular water. The resulting DNA concentration was again determined by Nanodrop.

Ligation of the digested, PCR created pGT232 fragment into the sticky blunt pSLER1 vector was done using the T4 DNA ligase from Thermoscientific per the following reaction.

| Ligation of pGT232fragment into pSLER1 for creation of pSLERGT |
| --- |
| 2 µl 10x T4 DNA ligase Buffer by ThermoScientific |
| 2 µl 50% PEG 4000 |
| 1 µl pSLER1 digested at 21 ng/µl |
| 5.5 µl pGT232 fragment digested at 6 ng/µl |
| 8.5 µl water |

Ligation reaction was at room temperature for 60 min. 5 µl of the ligation reaction was added to 50 µl of chemically competent Top10 DH5α *E. coli* from Life Technologies for transformation. Transformation was performed as described by the manufacterer. Transformation reaction was plated onto LB agar containing 50 µg/mL of ampicillin.

Colonies from the plates were sub-cultured in TB dry containing 300 µg/mL of erythromycin. These liquid cultures were used for the UltraClean 6 minute mini plasmid prep kit (MoBio). Plasmid samples were digested with ThermoScientific FastDigest NcoI and SalI, and the resulting digests were run on a 0.8% agarose 0.5% TBE with ethidium bromide gel to detect clones containing a plasmid with the pGT232 fragment insert.

The clone with successful insertion, the desired pSLERGT, was sent to BioBasic for sequencing. Once the sequencing verified the insert contained no mutations to alter function of the pGT232 fragment (SEQ ID NO:12), pSLERGT was transformed into 100-23C cells to verify functionality of the pGT232 segment in-vitro. pSLERGT successfully transformed 100-23 cells in addition to the *E. coli*, proving it a functional shuttle vector.

The reactants and conditions for electotrotransformation of the 100-23C cells are as described in M. A. McCONNELL et al., "Transfer of Plasmid pAMβ1 Between Members of the Normal Microflora Inhabiting the Murine Digestive Tract and Modification of the Plasmid in a *Lactobacillus reuteri* Host."

Briefly, a Gene Pulser™' apparatus (Bio-Rad Laboratories, Richmond, Calif.) will be used for all electroporation experiments described in this study. Recipient cells from overnight cultures at 37° C. in MRS broth will be used to inoculate MRS broth to an optical density of 0.06 at 600 nm (OD). Cultures will be incubated at 37° C. until an OD 600 of 0.8-1.0 is attained. The cells will be harvested by centrifugation, washed twice in electroporation buffer, and then resuspended in electroporation buffer at ¹⁄₂₀th of the original culture volume. Electroporation buffer consists of 952 mM sucrose-3.5 mM MgCl2 at pH 7.2 that has been filter sterilized.

Plasmid DNA, ≥1 µg, will be added to 0.4 ml of cells. This mixture is then placed in chilled sterile electroporation cuvettes (0.2 cm inter-electrode gap) and held on ice for 5 min. Following the application of a high-voltage electric pulse, voltage of 12,500 V/cm, 200 ohm parallel resistance, 25 µFD capacitance, the DNA-cell mixture is added to 10 mL of pre-warmed non-selective media for a 3 hour recovery period at 37° C. After recovery, cells are harvested by centrifugation and resuspended in 1 mL of media for plating. Approximately 50 ul of this solution will be plated onto selective media with 5 µg/mL of antibiotic. Diluted aliquots will also be plated on media without antibiotic to ensure cells remained viable throughout the procedure regardless of their plasmid uptake. After incubation of the plates in an anaerobe jar at 37° C. for approximately 40 h, colonies will be counted/utilized.

Colonies that grow will be positive for the plasmid, and these colonies will be grown in an MRS broth culture in the anaerobe jar with its gas pack components at 37° C. over night. Growth from these MRS overnight cultures will be our stock culture, and as such they will be prepared by using a 1:1 ratio of culture to 10% sterile skim milk and saved by freezing at −80° C.

The final shuttle vector pSLERGT was sent to BioBasic Inc. as mentioned above for ligation of the final FuzErmAvPAL or secFuzErmAvPAL into pSLERGT to create the therapeutic test vectors pHENOMM (SEQ ID NO:13) and pHENOMM-sec (SEQ ID NO:14) respectively.

The resulting plasmid (pHENOMM or pHENOMH) carried by *L. reuteri* are considered an embodiment of the present invention. Probiotic carrying pHENOMM or pHENOMH will be called PHEnominal. Strain specificity of the probiotic and plasmid used denotes its human or mouse usage. Stock vials of the appropriate strain will be thawed and cultured in MRS broth and anaerobic conditions at 37° C. overnight for in-vitro and in-vivo experimentation. A single vial of stock culture may be used for a long period of study by subculturing the most recent growth of PHEnominal.

EXAMPLE 2

Administration and Use of the Oral PHEnominal to Treat PKU

In certain embodiments, the genetically engineered probiotic to treat PKU described herein may be orally administered with food in mice and humans. Survival of the genetically modified probiotic to treat PKU ("PHEnominal") will be greater if it is ingested with food and this will be enhanced further if dairy is ingested concomitant with food. Modes of administration of the oral treatment are varied and may be in pill form, or powder/liquid form. The most appropriate form would be selected for the age and life stage of the patient (e.g. toddlers and infants often resist swallowing pills).

A patient may be provided with access to a phenylalanine monitor to determine levels of phe in the blood. As an essential amino acid, the patient must ensure they are not taking too much of the genetically engineered probiotic. Such phenylalanine monitors for home use are currently in clinical trials, though more expensive versions already exist (approximately $40,000.00 for the currently available machine).

EXAMPLE 3

Figure 2:
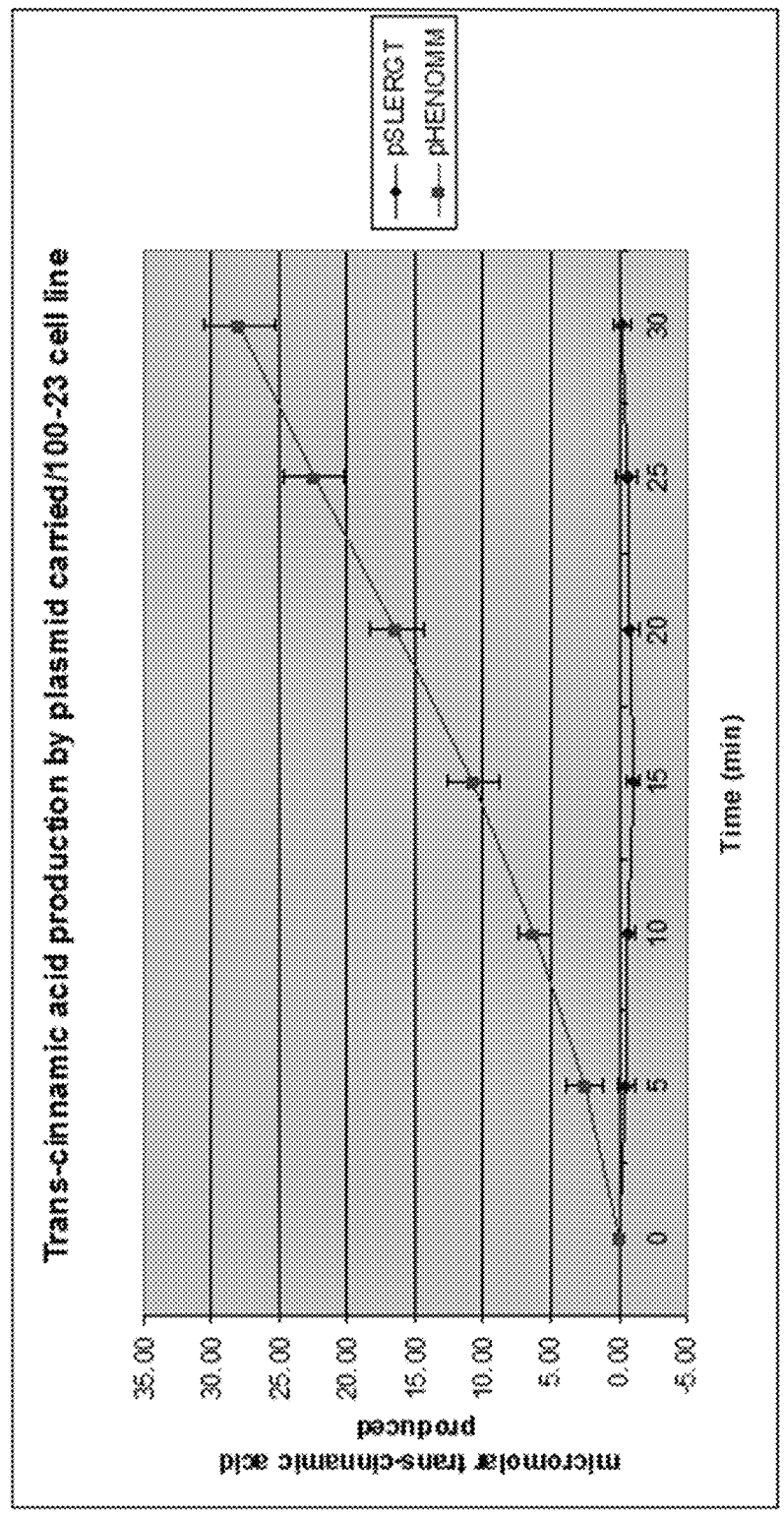
FIG. 2 shows trans-cinnamic acid production by plasmid carried/100-23 *L. reuteri* cell line in an embodiment of the present invention.

At this time, testing of mouse PHEnominal has been performed to demonstrate functional AvPAL enzyme within the cells. Lysate from 100-23 cells carrying pHENOMM (bearing the FuzErmAvPAL gene, non-secreted) plasmid contain far higher production of trans-cinnamic acid than lysate from cells carrying the empty vector pSLERGT. A representative set of results are seen in FIG. 2, and the data retains this trend over multiple experimental replicates. Values depicted indicate the amount of increase in absorbance readings at 280 nm, the absorbance point for trans-cinnamic acid/trans-cinnamate, in lysates given phosphate buffered saline with phenylalanine over the amount produced by cells only given phosphate buffered saline alone.

Subtracting the values for phosphate buffered saline alone from values measured in the presence of phenylalanine accounts for any increase to the absorbance created by other reactions. These results demonstrate *Lactobacillus reuteri* cells are capable of surviving while producing functional AvPAL enzyme.

EXAMPLE 4

Gene Construct Works Effectively in Other *Lactobacilli*

The species *Lactobacillus acidophilus* was used as the probiotic in this example. Two strains were tested. One strain (NCFM 56) was the parent unaltered strain of *Lactobacillus acidophilus* (obtained as *Lactobacillus acidophilus* NCFM®, from commercial sources). The other strain (NCFM 2605) was the parent strain (NCFM 56) with chromosomal insertion of the gene for AvPAL expression in *Lactobacilli* FuzErmAvPAL gene. As discussed above, the AvPAL gene described above with codon optimization for *Lactobacillus* expression was included, with expression driven by the ermB promoter. The presence of the AvPAL gene in the bacteria was verified by PCR.

Trans-cinnamic acid is one of two equimolar products produced by AvPAL as it cleaves phenylalanine. Trans-cinnamic acid production (as previously described) is detectable by an increase in absorbance at a light wavelength of 280 nm. Data collected was representative of three separate experimental growths. The assay was run as described in the examples above for the *Lactobacillus reuteri* 100-23 cells. Trans-cinnamate standard solutions were produced by dissolving trans-cinnamate in PBS to the desired concentration. Absorbance measurements for known concentrations of 0 µM, 6.25 µM, 12.5 µM, 25 µM, 50 µM, 100 µM, 200 µM, and 400 µM trans-cinnamate in PBS served as a standard curve. Unknown samples were quantified using this curve. A control of plain PBS for each cell line/condition was run to account for other cell processes causing an increased absorbance at 280 nm. This plain PBS control was subtracted from the PBS+phe for each sample to subtract non-trans-cinnamate metabolites that could increase the absorbance reading at 280 nm. Control and experimental *L. acidophilus* cells (NCFM 56 and NCFM 2605, respectively) were grown separately to the same OD600 in 25 mL of MRS media at 37° C. (OD600 0.600±0.750). Cells were chilled on ice for 5 minutes then centrifuged (9,000×g for 7 min, 4° C.). Cells were washed in 5 mL sterile chilled PBS and re-pelleted (9,000×g for 7 minutes at 4° C.). Supernatant was removed completely, and cells were re-suspended in 500 µl sterile chilled PBS for sonication on ice (four cycles, 40V, pulse 5 s on, 10 s off). Post sonication solutions were centrifuged (20,000×g for 15 minutes at 4° C.) to separate lysate and solids. 30 µl of the appropriate lysate was added to 150 µl PBS or 150 µl PBS with 12 mM phe (final concentrations of 0 mM phe and 10 mM phe respectively) for a total volume of 180 µl/well. Each condition was run in triplicate in a BioTek Synergy 2 plate reader at 37° C. using a 96 well UV transparent plate, an absorbance wavelength of 280 nm, and absorbance was measured at 5 minute intervals from t=0 to t=35 after allowing the plate to warm to 37° C. for 25 minutes in the machine. This assay was performed three separate times, each replicate utilizing a fresh growth of bacteria.

Figure 3:
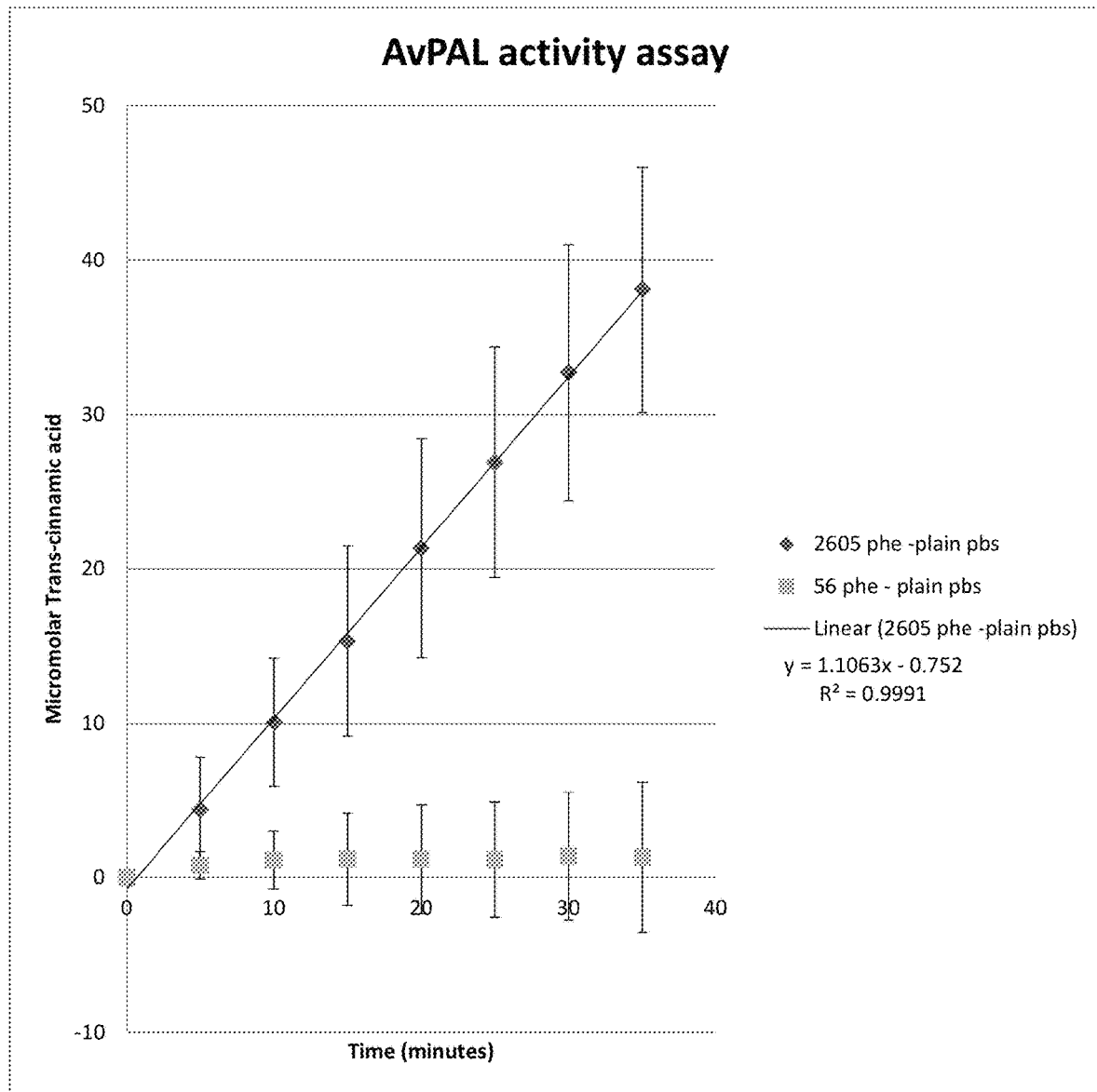
FIG. 3 shows trans-cinnamic acid production by chromosomally encoded AvPAL in *L. acidophilus* cell line in an embodiment of the present invention.

Prior to the start of each experiment, test wells were run to confirm the quantity of lysate used would not exceed the read limits of the machine. Dilution of lysate was performed if necessary while maintaining very similar total protein concentrations in control NCFM 56 lysate as compared to NCFM 2605 lysate. The total protein concentration of lysates was determined by Bradford protein assay. The results are shown in Tables 1-3 below and in FIG. 3.

TABLE 1

Median Values
Micromolar Trans-cinnamic acid

| Time | 2605 phe-plain pbs | 56 phe-plain pbs |
|---|---|---|
| 0 | 0 | 0 |
| 5 | 4.392123288 | 0.799086758 |
| 10 | 10.08561644 | 1.141552511 |
| 15 | 15.33390411 | 1.187214612 |
| 20 | 21.35273973 | 1.187214612 |
| 25 | 26.90924658 | 1.164383562 |
| 30 | 32.72260274 | 1.392694064 |
| 35 | 38.07363014 | 1.324200913 |

TABLE 2

Standard Deviations
Micromolar Trans-cinnamic acid

| Time | 2605 phe-plain pbs | 56 phe-plain pbs |
|---|---|---|
| 0 | 0 | 0 |
| 5 | 3.430002352 | 0.889532408 |
| 10 | 4.133654261 | 1.877595366 |
| 15 | 6.148998704 | 2.980724549 |
| 20 | 7.100734531 | 3.516752569 |
| 25 | 7.466636093 | 3.720130305 |
| 30 | 8.296709772 | 4.130918772 |
| 35 | 7.946554984 | 4.867674145 |

TABLE 3

P values

| Time | 2605 phe-plain pbs | 56 phe-plain pbs |
|---|---|---|
| 0 | 0 | 0 |
| 5 | 0.016976847 | 0.033953694 |
| 10 | 0.000246966 | 0.000493931 |
| 15 | 0.000162243 | 0.000324487 |
| 20 | 2.6916E−05 | 5.38319E−05 |
| 25 | 4.57846E−06 | 9.15692E−06 |
| 30 | 1.88935E−06 | 3.7787E−06 |
| 35 | 3.92211E−07 | 7.84422E−07 |

Values depicted indicate the amount of increase in absorbance readings at 280 nm, the absorbance point for trans-cinnamic acid/trans-cinnamate, in lysates given phosphate buffered saline with phenylalanine over the amount produced by cells only given phosphate buffered saline alone. Subtracting the values for phosphate buffered saline alone from values measured in the presence of phenylalanine accounts for any increase to the absorbance created by other reactions. These results demonstrate *Lactobacillus acidophilus* cells are capable of growing and producing functional AvPAL enzyme, just as *L. reuteri* cells are.

REFERENCES CITED

The following references, to the extent that they provide exemplary procedural or other details supplementary to those set forth herein, are specifically incorporated herein by reference.

Non-Patent Literature

Bourget, L, Chang, T. Phenylalanine ammonia-lyase immobilized in semipermeable mircrocapsules for enzyme replacement in phenylketonuria. *Federation of European Biochemical Societies,* 1985 vol 180 number 1 pp 5-9.

Bourget L, Chang T M S. *Biochim Biophys Acta.* 1986; 883:432-438

Safos S, Chang T M S. *Artif Cells Blood Substit Immobil Biotechnol.* 1995; 23:681-692

Sarkissian C N, Lee K C, Danagher P, Leung R, Fuller M A, Scriver C R. *Am J Hum Genet Suppl.* 1996; 59:1183. (abstr.).

Sarkissian C N, Shao Z, Blain F, Peevers R, Su H, Fuller M A, Scriver C R. *Am J Hum Genet Suppl.* 1997; 61:182. (abstr.).

Liu et al. Study on a Novel Strategy to Treatment of Phenylketonuria. *Artif cells, Blood Substit Immobil Biotechnol,* 2002, 30(4), 243-257.

http://www.pkunsw.org.au/research-blog-full-article

M. A. McCONNELL et al., "Transfer of Plasmid pAMβ1 Between Members of the Normal Microflora Inhabiting the Murine Digestive Tract and Modification of the Plasmid in a *Lactobacillus reuteri* Host"

---

What is claimed:

1. A composition for treating phenylketonuria, comprising:
a probiotic bacterium from the *Lactobacillus* genera selected from the group consisting of *Lactobacillus acidophilus, Lactobacillus brevis, Lactobacillus casei, Lactobacillus plantarum*, and *Lactobacillus reuteri*, wherein the probiotic bacterium is genetically modified to express an exogenous nucleotide sequence encoding a functional phenylalanine ammonia-lyase (PAL) enzyme protein, and wherein the nucleotide sequence encoding the phenylalanine ammonia-lyase (PAL) comprises SEQ ID NO:15.

2. The composition of claim 1, wherein the nucleotide sequence encoding the phenylalanine ammonia-lyase (PAL) is integrated into the chromosome of the probiotic bacterium.

3. The composition of claim 1, wherein the probiotic bacterium carries a recombinant plasmid vector comprising the nucleotide sequence encoding the phenylalanine ammonia-lyase (PAL), and wherein the recombinant plasmid vector comprises a nucleotide sequence comprising SEQ ID NO: 13 or SEQ ID NO:14.

4. The composition of claim 1, wherein the probiotic bacterium is *Lactobacillus reuteri*.

5. The composition of claim 1, wherein the probiotic bacterium is *Lactobacillus acidophilus*.

6. A method for administering a composition for treating phenylketonuria, comprising the step of:
administering a therapeutically effective amount of the composition of claim 1 to a patient in need thereof, wherein said administration is oral.

7. A composition for treating phenylketonuria, comprising:
a probiotic bacterium, wherein the probiotic bacterium is *Lactobacillus acidophilus*, wherein the probiotic bacterium is genetically modified to integrate an exogenous nucleotide sequence encoding a functional phenylalanine ammonia-lyase (PAL) enzyme protein into the chromosome of the probiotic bacterium, wherein the probiotic bacterium expresses the nucleotide sequence encoding the phenylalanine ammonia-lyase (PAL), and wherein the nucleotide sequence encoding the phenylalanine ammonia-lyase (PAL) comprises SEQ ID NO: 15.

* * * * *

UNITED STATES PATENT AND TRADEMARK OFFICE
CERTIFICATE OF CORRECTION

PATENT NO. : 10,744,168 B2
APPLICATION NO. : 15/800529
DATED : August 18, 2020
INVENTOR(S) : Katherine Durrer et al.

It is certified that error appears in the above-identified patent and that said Letters Patent is hereby corrected as shown below:

In the Specification

1. In Column 5, Line 21, delete "nipl," and insert -- nlpl, --, therefor.
2. In Column 5, Line 22, delete "snub." and insert -- mub. --, therefor.
3. In Column 5, Line 57, delete "probioitic" and insert -- probiotic --, therefor.
4. In Column 9, Line 20, delete "manufacterer." and insert -- manufacturer. --, therefor.
5. In Column 9, Line 38, delete "electotrotransformation" and insert -- electrotransformation --, therefor.
6. In Column 9, Line 54, delete "MgCI2" and insert -- MgCI2 --, therefor.

In the Claims

7. In Column 54, Line 7, in Claim 6, delete "administering a therapeutically effective amount of the" and insert -- administering the --, therefor.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 15

<210> SEQ ID NO 1
<211> LENGTH: 14
<212> TYPE: DNA
<213> ORGANISM: Artificial Sequence
<220> FEATURE:
<223> OTHER INFORMATION: Sequence to be added to to front of codon
      optimized AvPAL sequence.

<400> SEQUENCE: 1
aggagtaggt ataa                                                     14

<210> SEQ ID NO 2
<211> LENGTH: 56
<212> TYPE: DNA
<213> ORGANISM: Artificial Sequence
<220> FEATURE:
<223> OTHER INFORMATION: Sequence to be added to the end of AvPAL
      sequence.

<400> SEQUENCE: 2
tgataagtta agggtgcat aaactgcatc ccttaactta tcaaaaaaaa gtcgac        56

<210> SEQ ID NO 3
<211> LENGTH: 1777
<212> TYPE: DNA
<213> ORGANISM: Artificial Sequence
<220> FEATURE:
<223> OTHER INFORMATION: Synthesized AvPAL 5' to 3'

<400> SEQUENCE: 3
aggagtaggt ataaatgaag actttatctc aagcacaatc taagactagt tctcaacaat    60
tctcatttac tggaaactca agtgctaatg ttatcattgg taatcaaaag cttactatta   120
acgatgttgc acgggttgca cgcaatggta ctttagttag tttaactaac aacactgaca   180
ttttacaagg cattcaagct agttgcgact atatcaataa cgctgttgaa tcaggagaac   240
caatttatgt tgttacttca ggattcggtg gaatggcaaa cgtcgctatt agtcgtgaac   300
aagcttctga acttcaaact aatcttgttt ggtttcttaa aacaggagct ggtaataaac   360
ttccattagc agatgttcgt gctgctatgt tattacgtgc aaattcacac atgcgtggcg   420
cttctggtat tcgtcttgaa ttaattaagc gtatggaaat tttccttaac gccggtgtta   480
caccttatgt ttacgaattc ggatcaattg gtgcaagtgg agatcttgtt ctttatctt   540 atattacagg ttctttaatt ggtttggatc catcattcaa agttgatttt aatggtaaag   600
aaatggatgc cccaacagct cttcgacaat taaatttatc accacttaca ttacttccaa   660
aagaaggtct tgctatgatg aatggtacat cagttatgac gggaattgct gctaattgcg   720
```

```
tttatgatac tcaaattctt actgctattg ccatgggtgt tcatgcctta gatattcaag    780
cacttaatgg cacaaatcaa agtttccacc cattcattca caattctaaa cctcacccag    840
gtcaactttg ggctgctgat caaatgattt ctcttttagc taatagtcaa cttgttcgcg    900
acgaattaga tggtaagcat gattatcgtg atcatgaact tattcaagac cgctatagtt    960
tacgttgctt accacaatat ttgggtccta ttgttgatgg aatttcacaa attgctaagc   1020
aaattgaaat cgaaattaat agtgtcactg acaatccatt aattgacgtt gataaccaag   1080
cctcatacca tggcggtaac ttttgggtc aatatgttgg catgggcatg gaccacttac    1140
gttactacat tggtcttctt gcaaagcatt tggatgtcca aattgcactt ttggccagtc   1200
cagaattcag taacggactt ccaccatcat tattgggaaa ccgggaacga aggtaaaaca   1260
tgggtcttaa gggtttgcaa atttgtggca actcaattat gccattgttg acttttacg    1320 gaaattcaat tgctgatcgc tttcctacac acgccgaaca atttaaccaa atattaact    1380 ctcaaggata cacttctgct acgttagcac gacggtctgt tgatattttt caaaactacg   1440
tagctattgc attaatgttt ggagtacaag ctgttgattt acggacttac aaaaagacgg   1500
gccattatga tgctcgtgct tgtttaagtc cagctacaga acgtctttat tcagcagtac   1560
gtcatgttgt cggccaaaaa cctacatcag atcggccata tatttggaac gataacgaac   1620
aaggacttga cgaacatatt gctcgtattt ctgctgatat cgctgctggt ggtgtaattg   1680
ttcaagccgt acaagatatc cttccttgtt tacactaata atgataagtt aagggggtgca  1740 taaactgcat cccttaactt atcaaaaaaa agtcgac                            1777

<210> SEQ ID NO 4
<211> LENGTH: 186
<212> TYPE: DNA
<213> ORGANISM: Artificial Sequence
<220> FEATURE:
<223> OTHER INFORMATION: Synthetic ErmB promoter sequence

<400> SEQUENCE: 4
gcatgctagc tatagttcta gaggatacct ggttgattaa cgttagcctg gctacgtata     60
ctcctggaag tattaataga cgacctagga tgcatatgtt caagagtgtg ttgatagtgc    120
agtatcttaa aattttgtat aataggaatt gaagttaaat tagatgctaa aaattttgtaa   180 ttaaga                                                              186

<210> SEQ ID NO 5
<211> LENGTH: 129
<212> TYPE: DNA
<213> ORGANISM: Artificial Sequence
<220> FEATURE:
<223> OTHER INFORMATION: Secretion tag sequence

<400> SEQUENCE: 5
atgtatactg aaaatacagg taaacatcac cgtaacggac ttcctgtgtg gctattacca     60
ttattggtcg ttattagttt ttggggcgta agccaaaata ttatggttgt tgatgcttct    120
tcagttgat                                                           129

<210> SEQ ID NO 6
<211> LENGTH: 2092
<212> TYPE: DNA
<213> ORGANISM: Artificial Sequence
<220> FEATURE:
<223> OTHER INFORMATION: Full secFuzErmAvPAL sequence

<400> SEQUENCE: 6
```

-continued

```
gcatgctagc tatagttcta gaggatacct ggttgattaa cgttagcctg gctacgtata      60
ctcctggaag tattaataga cgacctagga tgcatatgtt caagagtgtg ttgatagtgc     120
agtatcttaa aattttgtat aataggaatt gaagttaaat tagatgctaa aaatttgtaa    180
ttaagaagga gtaggtataa atgtatactg aaaatacagg taaacatcac cgtaacggac    240
ttcctgtgtg gctattacca ttattggtcg ttattagttt ttgggcgta agccaaaata     300
ttatggttgt tgatgcttct tcagttgata tgaagacttt atctcaagca caatctaaga    360
ctagttctca acaattctca tttactggaa actcaagtgc taatgttatc attggtaatc    420
aaaagcttac tattaacgat gttgcacggg ttgcacgcaa tggtacttta gttagtttaa    480
ctaacaacac tgacatttta caaggcattc aagctagttg cgactatatc aataacgctg    540
ttgaatcagg agaaccaatt tatggtgtta cttcaggatt cggtggaatg gcaaacgtcg    600
ctattagtcg tgaacaagct tctgaacttc aaactaatct tgtttggttt cttaaaacag    660
gagctggtaa taaacttcca ttagcagatg ttcgtgctgc tatgttatta cgtgcaaatt    720
cacacatgcg tggcgcttct ggtattcgtc ttgaattaat taagcgtatg gaaattttcc    780
ttaacgccgg tgttacacct tatgtttacg aattcggatc aattggtgca gtggagatc     840
ttgttccttt atcttatatt acaggttctt taattggttt ggatccatca ttcaaagttg    900
attttaatgg taaagaaatg gatgccccaa cagctcttcg acaattaaat ttatcaccac    960
ttacattact tccaaaagaa ggtcttgcta tgatgaatgg tacatcagtt atgacgggaa   1020
ttgctgctaa ttgcgtttat gatactcaaa ttcttactgc tattgccatg ggtgttcatg   1080
ccttagatat tcaagcactt aatggcacaa atcaaagttt ccacccattc attcacaatt   1140
ctaaacctca cccaggtcaa ctttgggctg ctgatcaaat gatttctctt ttagctaata   1200
gtcaacttgt tcgcgacgaa ttagatggta agcatgatta tcgtgatcat gaacttattc   1260
aagaccgcta tagtttacgt tgcttaccac aatatttggg tcctattgtt gatggaattt   1320
cacaaattgc taagcaaatt gaaatcgaaa ttaatagtgt cactgacaat ccattaattg   1380
acgttgataa ccaagcctca taccatggcg gtaacttttt gggtcaatat gttggcatgg   1440
gcatggacca cttacgttac tacattggtc ttcttgcaaa gcatttggat gtccaaattg   1500
cactttggc cagtccagaa ttcagtaacg gacttccacc atcattattg ggaaaccggg    1560
aacgaaaggt aaacatgggt cttaagggtt tgcaaatttg tggcaactca attatgccat   1620
tgttgacttt ttacggaaat tcaattgctg atcgctttcc tacacacgcc gaacaattta   1680
accaaaatat taactctcaa ggatacactt ctgctacgtt agcacgacgg tctgttgata   1740
ttttttcaaaa ctacgtagct attgcattaa tgtttggagt acaagctgtt gatttacgga   1800
cttacaaaaa gacgggccat tatgatgctc gtgcttgttt aagtccagct acagaacgtc   1860
tttattcagc agtacgtcat gttgtcggcc aaaaacctac atcagatcgg ccatatattt   1920
ggaacgataa cgaacaagga cttgacgaac atattgctcg tatttctgct gatatcgctg   1980
ctggtggtgt aattgttcaa gccgtacaag atatccttcc ttgtttacac taataatgat   2040
aagttaaggg gtgcataaac tgcatccctt aacttatcaa aaaaaagtcg ac           2092
```

<210> SEQ ID NO 7
<211> LENGTH: 7068
<212> TYPE: DNA
<213> ORGANISM: Artificial Sequence
<220> FEATURE:
<223> OTHER INFORMATION: pSLERGT sequence

<400> SEQUENCE: 7

```
tcttccgctt cctcgctcac tgactcgctg cgctcggtcg ttcggctgcg gcgagcggta      60
tcagctcact caaaggcggt aatacggtta tccacagaat cagggggataa cgcaggaaag    120
aacatgtgag caaaaggcca gcaaaaggcc aggaaccgta aaaaggccgc gttgctggcg    180
ttttttccata ggctccgccc ccctgacgag catcacaaaa atcgacgctc aagtcagagg    240
tggcgaaacc cgacaggact ataaagatac caggcgtttc ccctggaag ctccctcgtg     300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccc gttcagcccg accgctgcgc cttatccggt     480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatcttt ctacggggtc tgacgctcag tggaacgaaa actcacgtta agggattttg     840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc ttttttcaata ttattgaagc atttatcagg gttattgtct catgagcgga   1860
tacatatttg aatgtattta gaaaaataaa caaataggg ttccgcgcac atttccccga    1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc ggagacggt cacagcttgt ctgtaagcgg atgccgggag cagacaagcc    2100
cgtcagggcg cgtcagcggg tgttggcggg tgtcggggct ggcttaacta tgcggcatca   2160
gagcagattg tactgagagt gcaccataaa attgtaaacg ttaatatttt gttaaaattc   2220
gcgttaaatt tttgttaaat cagctcattt tttaaccaat aggccgaaat cggcaaaatc   2280
ccttataaat caaaagaata gcccgagata gggttgagtg ttgttccagt ttggaacaag   2340
```

```
agtccactat taaagaacgt ggactccaac gtcaaagggc gaaaaaccgt ctatcagggc   2400
gatggcccac tacgtgaacc atcacccaaa tcaagttttt tggggtcgag gtgccgtaaa   2460
gcactaaatc ggaaccctaa agggagcccc cgatttagag cttgacgggg aaagccggcg   2520
aacgtggcga gaaaggaagg gaagaaagcg aaaggagcgg gcgctagggc gctggcaagt   2580
gtagcggtca cgctgcgcgt aaccaccaca cccgccgcgc ttaatgcgcc gctacagggc   2640
gcgtactatg gttgctttga cgtatgcggt gtgaaatacc gcacagatgc gtaaggagaa   2700
aataccgcat caggcgccat tcgccattca ggctgcgcaa ctgttgggaa gggcgatcgg   2760
tgcgggcctc ttcgctatta cgccagctgg cgaaaggggg atgtgctgca aggcgattaa   2820
gttgggtaac gccagggttt tcccagtcac gacgttgtaa aacgacggcc agtgaattcg   2880
aatggccatg gaggatttat tctctccgca gttttgagct taatcgtctc attaactact   2940
gcacttttct ccgattggct tcgtcggaga aaataatcta acggcatgaa gcgcaaatta   3000
aaagccactc aactatgggc ctagttgggt ggcttttttg caaccattac ggttttactt   3060
ctctataaga attatagcat caatcttcat cattagccaa ctcaatagaa gctcgatata   3120
gatcatgttg agctttatcc aagctatcta aaagttcgcc ataaatatca atattttcct   3180
tttcagcaac caattttttc aaatcttgaa gattatcagc aatctgttct gccataactc   3240
catagatttc agcttgtttc ttcatattgt caattgtctt aatatcttgt aactccattc   3300
ctatcactcc catcttacat agttacttac cttagaattc aacgatata tcacagtatc   3360 tacaacatca tctttttctt tttcgtcatc cacattaatt agatcatctt cttttccgtc   3420
cagcaataac tcatgatgaa tctcttttag taatcccgca aagcttaatt gtcgagttcc   3480
agccagagca tgctcgagct cgtcaacaac aactaaatcg cctttctcat catccgtaat   3540
ataatcataa tctttaactt gatatttact tacttctttt gccgaagcaa tcaaactatt   3600
atcttttttt gacgcccgaa ttttcttgat attaacaatc ggcttgtagt ctaatttcct   3660
tgctcgcttc cataattgtg accaattctc ttgggtaaga taatgaccct tagaaaaata   3720
actagatttc accattaaca aaatatgtac atgttgatgg aaagttagac tatctcgatt   3780
gaccgttatt tctgtagatc gcacataacc aagaagatct ttttttacat ctttatattg   3840
aaaaagccga taaattgaac gattcatcga agtaagattt tttctaagct cgcccaactt   3900
tgagctttcc tcagttaatg tcaagaacag aaatatagca ctaggatcct ttttatatgc   3960
tgtatctaaa atttgacgca actcataaga attttttcatc gatcggcgcc agctacataa   4020
tggacaaagt ctcgaatgac aaaaccacgt ttgatataac tttaaccat tatcagtttt   4080 cgcaaattga agaacttctc cgcactttga aacgttatga gcttttttaa aatttaaaac   4140
ctccagatat tgggaataag ttaagttagc aagtttttc tgcttccacg gtctaacttt   4200
cccattacta gaggtatctt ttagaatttc tttttatac atttcttata cctctaactg   4260
caaaaactac aagcagtcag agttagttat cattgatata ttcctaatga catattataa   4320
tagggttcga agttaataac gataactaac tcatgcatcg acggccaaat cgaacaactg   4380
catgagtttt ttatttaatt cttacaatgc ttattataca ccaaaaagtg ttatatttta   4440
aaatcctaat aaacccagtc atatcaaggg tttaacccaa tttcaaaaaa tggcgttgtt   4500
tctatatgta tcaagataag aagaaactcg cttacagcga gtttctaaat aggggtttca   4560
cccctaaaac cctgaccagc tgagccagct ggaccgcatt tccctcgcc gggcgggcgt   4620 aaagcggaaa aaatgacttt tttctcgctt tcgctcaact agggtcttcc cgtctcacca   4680
```

```
tgtcaagcgc tgcccttccg ctacgctcca ggcgtttgtc gcttgacact cacctactaa    4740
cagcgggctt cgccaccagt ctactatctg caacacggca acaagattaa tcagaatatg    4800
cattgaagca gtgcgctccg ctccttgtct tgcgacaaag cgagcgcact gcttcaatgc    4860
ttttttattt tctgaattcc ataactcgat aattagaaaa agttagtccg ttagaaacgt    4920
ctgccacgcc gaggaagtca ttccagtttg accactcaaa tcatcagcga catcattgag    4980
ataatcaatc agcaatttttc tagtttctat ctgctttgga attttttacca cagccaaaat    5040 tgagtcccac ttagcaatca caaagatttt tctgacggct ttattagcct tttccgcact    5100 aatattttc gctttatctc gtttattttg atcggtcgat ggtatccgat cgactgttgt    5160
tacagcattt gacgcaggtt gctagataaa cgactagacc gaataatttt tattccaact    5220
atttttgcaa ccaaaaaaat cacaaaataa tcaaccaata aaacgataac taacttcttg    5280
ctacatccga ttaattttc tccagcctgc cagaaatcgg cccaaatatt gaaatattga    5340
ggaaattttg ggctgaaaaa acattaatt ttttcggcaa acaagccaac acagccaagc    5400
agaaaagcta agaaaataag ttccagccaa ttaaaaaatc gccacgaaag agaaaaaaat    5460
cggtcaaaat aaatcgaact tgatttcatt ttctagcccc cgaagtcttc gataaacggc    5520
gccataaaag gaactacacg gttttccggt tgagtacttg caagccctaa ccccttagaa    5580
aagccgtcat gattaacaac tgttgtcgac tcagctaggg ccctatatat ggatccaatt    5640
gcaatgatca tcatgacaga tctgcgcgcg atcgatatca gcgctttaaa tttgcgcatg    5700
ctagctatag ttctagaggt accggttgtt aacgttagcc ggctacgtat actccggaat    5760
attaataggc ctaggatgca tatgcttaga agcaaactta agagtgtgtt gatagtgcag    5820
tatcttaaaa ttttgtataa taggaattga agttaaatta gatgctaaaa atttgtaatt    5880
aagaaggagt gattacatga acaaaaatat aaaatattct caaaactttt taacgagtga    5940
aaaagtactc aaccaaataa taaacaatt gaatttaaaa gaaaccgata ccgtttacga    6000
aattggaaca ggtaaagggc atttaacgac gaaactggct aaaataagta aacaggtaac    6060
gtctattgaa ttagacagtc atctattcaa cttatcgtca gaaaaattaa aactgaatac    6120
tcgtgtcact ttaattcacc aagatattct acagtttcaa ttccctaaca acagaggta    6180 taaaattgtt gggagtattc cttaccattt aagcacacaa attattaaaa aagtggtttt    6240
tgaaagccat gcgtctgaca tctatctgat tgttgaagaa ggattctaca agcgtacctt    6300
ggatattcac cgaacactag ggttgctctt gcacactcaa gtctcgattc agcaattgct    6360
taagctgcca gcggaatgct ttcatcctaa accaaaagta acagtgtct taataaaact    6420 taccgccat accacagatg ttccagataa atattggaag ctatatacgt actttgtttc    6480
aaaatgggtc aatcgagaat atcgtcaact gtttactaaa aatcagtttc atcaagcaat    6540
gaaacacgcc aaagtaaaca atttaagtac cgttacttat gagcaagtat tgtctatttt    6600
taatagttat ctattattta acgggaggaa ataattctat gagtcgcttt tgtaaatttg    6660
gaaagttaca cgttactaaa gggaatgtag ataaattatt aggtatacta ctgacagctt    6720
ccaagcatat ggcggccgcc tgcagctggc gccatcgata cgcgtacgtc gcgaccgcgg    6780
acatgtacag agctcgagaa gtactagtgg ccacgtgggc cgtgcacctt aagcttggcg    6840
taatcatggt catagctgtt tcctgtgtga aattgttatc cgctcacaat tccacacaac    6900
atacgagccg gaagcataaa gtgtaaagcc tggggtgcct aatgagtgag ctaactcaca    6960
ttaattgcgt tgcgctcact gcccgctttc cagtcgggaa acctgtcgtg ccagctgcat    7020
taatgaatcg gccaacgcgc ggggagaggc ggtttgcgta ttgggcgc                 7068
```

<210> SEQ ID NO 8
<211> LENGTH: 2764
<212> TYPE: DNA
<213> ORGANISM: Artificial Sequence
<220> FEATURE:
<223> OTHER INFORMATION: Predicted pGT232 from PCR of pNCKH103

<400> SEQUENCE: 8

```
tagctgagtc gacaacagtt gttaatcatg acggcttttc taaggggtta gggcttcaag      60
tactcaaccg gaaaaccgtg tagttccttt tatggcgccg tttatcgaag acttcggggg     120
ctagaaaatg aaatcaagtt cgatttattt tgaccgattt ttttctcttt cgtggcgatt     180
ttttaattgg ctggaactta ttttcttagc ttttctgctt ggctgtgttg gcttgtttgc     240
cgaaaaaatt aatgtttttt tcagcccaaa atttcctcaa tatttcaata tttgggccga     300
tttctggcag gctggagaaa aattaatcgg atgtagcaag aagttagtta tcgttttatt     360
ggttgattat tttgtgattt ttttggttgc aaaaatagtt ggaataaaaa ttattcggtc     420
tagtcgttta tctagcaacc tgcgtcaaat gctgttaaca acagtcgatc ggataccatc     480
gaccgatcaa aataaacgag ataaagcgaa aaatattagt gcggaaaagg ctaataaagc     540
cgtcagaaaa tcttttgtga ttgctaagtg ggactcaatt ttggctgtgg taaaaattcc     600
aaagcagata gaaactagaa aattgctgat tgattatctc aatgatgtcg ctgatgattt     660
gagtggtcaa actggaatga cttcctcggc gtggcagacg tttctaacgg actaactttt     720
tctaattatc gagttatgga attcagaaaa taaaaaagca ttgaagcagt gcgctcgctt     780
tgtcgcaaga caaggagcgg agcgcactgc ttcaatgcat attctgatta atcttgttgc     840
cgtgttgcag atagtagact ggtgcgaagc ccgctgttag taggtgagtg tcaagcgaca     900
caacgcctgg agcgtgagcg aagggcagc gcttgacatg gtgagacggg aagaccctag      960
ttgagcgaaa gcgagaaaaa agtcatttt tccgctttag cccgcccggc gaggggaaat     1020
gcggtccagc tgggtcaggg ttttagggg tgaaacatcc ttagaaactc gctgtaagcg     1080
agtttcttct tatcttgata catatagaaa caacgccatt ttttgaaatt gggttaaacc     1140
cttgatatga ctgggtttat taggatttta aaatataaca cttttttggtg tataataagc     1200
attgtaagaa ttaaataaaa aactcatgca gttgttcgat ttggccgtcg atgcatcagt     1260
tagttatcgt tattaacttc gaaccctatt ataatatgtc attaggaata tatcaatgat     1320
aactaactct gactgcttgt agttttttgca gttagaggta taagaaatgt ataaaaaga     1380
aattctaaaa gatacctcta gtaatgggaa agttagaccg tggaagcaga aaaaacttgc     1440
taacttaact tattcccaat atctggaggt tttaaatttt aaaaaagctc ataacgtttc     1500
aaagtgcgga gaagttcttc aatttgcgaa aactgataat ggtttaaagt tatatcaaac     1560
gtggttttgt cattcgagac tttgtccatt atgtagctgg cgccgatcga tgaaaaattc     1620
ttatgagttg cgtcaaattt tagatacagc atataaaaag gatcctagtg ctatatttct     1680
cttcttgaca ttaactgagg aaagctcaaa gttgggcgag cttagaaaaa atcttacttc     1740
gatgaatcgt tcaatttatc ggcttttttca atataaagat gtaaaaaaag atcttcttgg     1800
ttatgtgcga tctacagaaa taacggtcaa tcgagatagt ctaactttcc atcaacatgt     1860
acatattttg ttaatggtga atctagtta ttttctaag ggtcattatc ttacccaaga      1920
gaattggtca caattatgga agcgagcaag gaaattagac tacaagccga ttgttaatat     1980
caagaaaatt cgggcgtcaa aaaaagataa tagtttgatt gcttcggcaa aagaagtaag     2040
```

-continued

```
taaatatcaa gttaaagatt atgattatat tacggatgat gagaaaggcg atttagttgt    2100
tgttgacgag ctcgagcatg ctctggctgg aactcgacaa ttaagctttg cgggattact    2160
aaaagagatt catcatgagt tattgctgga cgaaaaagaa gatgatctaa ttaatgtgga    2220
tgacgaaaaa gaaaaagatg atgttgtaga tactgtgata tatcgttgga attctaaggt    2280
aagtaactat gtaagatggg agtgatagga atggagttac aagatattaa gacaattgac    2340
aatatgaaga aacaagctga aatctatgga gttatgccag aacagattgc tgataatctt    2400
caagatttga aaaaattggt tgctgaaaag aaaaatattg atatttatgg cgaactttta    2460
gatagcttgg ataaagctca acatgatcta tatcgagctt ctattgagtt ggctaatgat    2520
gaagattgat gctataattc ttatagagaa gtaaaaccgt aatggttgca aaaaagccac    2580
ccaactaggc ccatagttga gtggctttta atttgcgctt catgccgtta gattattttc    2640
tccgacgaag ccaatcggag aaaagtgcag tagttaatga gacgattaag ctcaaaactg    2700
cggagagaat aaatcctcca tggtttctta gacggagaga ataaatcctc catggtttct    2760
taga                                                                 2764
```

<210> SEQ ID NO 9
<211> LENGTH: 4356
<212> TYPE: DNA
<213> ORGANISM: Artificial Sequence
<220> FEATURE:
<223> OTHER INFORMATION: pSLER1 sequence

<400> SEQUENCE: 9

```
tcttccgctt cctcgctcac tgactcgctg cgctcggtcg ttcggctgcg gcgagcggta      60
tcagctcact caaaggcggt aatacggtta tccacagaat caggggataa cgcaggaaag     120
aacatgtgag caaaaggcca gcaaaaggcc aggaaccgta aaaaggccgc gttgctggcg     180
tttttccata ggctccgccc cctgacgagc atcacaaaaa tcgacgctc aagtcagagg      240 tggcgaaacc cgacaggact ataaagatac caggcgtttc cccctggaag ctccctcgtg     300
cgctctcctg ttccgaccct gccgcttacc ggatacctgt ccgcctttct cccttcggga     360
agcgtggcgc tttctcatag ctcacgctgt aggtatctca gttcggtgta ggtcgttcgc     420
tccaagctgg gctgtgtgca cgaaccccc gttcagcccg accgctgcgc cttatccggt      480
aactatcgtc ttgagtccaa cccggtaaga cacgacttat cgccactggc agcagccact     540
ggtaacagga ttagcagagc gaggtatgta ggcggtgcta cagagttctt gaagtggtgg     600
cctaactacg gctacactag aagaacagta tttggtatct gcgctctgct gaagccagtt     660
accttcggaa aaagagttgg tagctcttga tccggcaaac aaaccaccgc tggtagcggt     720
ggtttttttg tttgcaagca gcagattacg cgcagaaaaa aaggatctca agaagatcct     780
ttgatctttt ctacggggtc tgacgctcag tggaacgaaa actcacgtta agggattttg     840
gtcatgagat tatcaaaaag gatcttcacc tagatccttt taaattaaaa atgaagtttt     900
aaatcaatct aaagtatata tgagtaaact tggtctgaca gttaccaatg cttaatcagt     960
gaggcaccta tctcagcgat ctgtctattt cgttcatcca tagttgcctg actccccgtc    1020
gtgtagataa ctacgatacg ggagggctta ccatctggcc ccagtgctgc aatgataccg    1080
cgagacccac gctcaccggc tccagattta tcagcaataa accagccagc cggaagggcc    1140
gagcgcagaa gtggtcctgc aactttatcc gcctccatcc agtctattaa ttgttgccgg    1200
gaagctagag taagtagttc gccagttaat agtttgcgca acgttgttgc cattgctaca    1260
ggcatcgtgg tgtcacgctc gtcgtttggt atggcttcat tcagctccgg ttcccaacga    1320
```

```
tcaaggcgag ttacatgatc ccccatgttg tgcaaaaaag cggttagctc cttcggtcct    1380
ccgatcgttg tcagaagtaa gttggccgca gtgttatcac tcatggttat ggcagcactg    1440
cataattctc ttactgtcat gccatccgta agatgctttt ctgtgactgg tgagtactca    1500
accaagtcat tctgagaata gtgtatgcgg cgaccgagtt gctcttgccc ggcgtcaata    1560
cgggataata ccgcgccaca tagcagaact ttaaaagtgc tcatcattgg aaaacgttct    1620
tcggggcgaa aactctcaag gatcttaccg ctgttgagat ccagttcgat gtaacccact    1680
cgtgcaccca actgatcttc agcatctttt actttcacca gcgtttctgg gtgagcaaaa    1740
acaggaaggc aaaatgccgc aaaaaaggga ataagggcga cacggaaatg ttgaatactc    1800
atactcttcc ttttcaata ttattgaagc atttatcagg gttattgtct catgagcgga    1860
tacatatttg aatgtattta gaaaaataaa caaatagggg ttccgcgcac atttccccga    1920
aaagtgccac ctgacgtcta agaaaccatt attatcatga cattaaccta taaaaatagg    1980
cgtatcacga ggcccttcg tctcgcgcgt ttcggtgatg acgtgaaaa cctctgacac    2040 atgcagctcc cggagacggt cacagcttgt ctgtaagcgg atgccgggag cagacaagcc    2100
cgtcagggcg cgtcagcggg tgttggcggg tgtcggggct ggcttaacta tgcggcatca    2160
gagcagattg tactgagagt gcaccataaa attgtaaacg ttaatatttt gttaaaattc    2220
gcgttaaatt tttgttaaat cagctcattt tttaaccaat aggccgaaat cggcaaaatc    2280
ccttataaat caaagaata gcccgagata gggttgagtg ttgttccagt ttggaacaag    2340
agtccactat taagaacgt ggactccaac gtcaaagggc gaaaaaccgt ctatcagggc    2400
gatggcccac tacgtgaacc atcacccaaa tcaagttttt tggggtcgag gtgccgtaaa    2460
gcactaaatc ggaaccctaa agggagcccc cgatttagag cttgacgggg aaagccggcg    2520
aacgtggcga gaaaggaagg gaagaaagcg aaaggagcgg gcgctagggc gctggcaagt    2580
gtagcggtca cgctgcgcgt aaccaccaca cccgccgcgc ttaatgcgcc gctacagggc    2640
gcgtactatg gttgctttga cgtatgcggt gtgaaatacc gcacagatgc gtaaggagaa    2700
aataccgcat caggcgccat tcgccattca ggctgcgcaa ctgttgggaa gggcgatcgg    2760
tgcgggcctc ttcgctatta cgccagctgg cgaaagggg atgtgctgca aggcgattaa    2820
gttgggtaac gccagggttt tcccagtcac gacgttgtaa aacgacggcc agtgaattcg    2880
aatggccatg gacgtcgac ctgaggtaat tataacccgg gccctatata tggatccaat    2940
tgcaatgatc atcatgacag atctgcgcgc gatcgatatc agcgctttaa atttgcgcat    3000
gctagctata gttctagagg taccggttgt taacgttagc cggctacgta tactccggaa    3060
tattaatagg cctaggatgc atatgttaag agtgtgttga tagtgcagta tcttaaaatt    3120
ttgtataata ggaattgaag ttaaattaga tgctaaaaat ttgtaattaa gaggagtga    3180 ttacatgaac aaaaatataa aatattctca aaactttta acgagtgaaa aagtactcaa    3240
ccaaataata aaacaattga atttaaaaga accgatacc gtttacgaaa ttggaacagg    3300
taaagggcat ttaacgacga aactggctaa aataagtaaa caggtaacgt ctattgaatt    3360
agacagtcat ctattcaact tatcgtcaga aaaattaaaa ctgaatactc gtgtcacttt    3420
aattcaccaa gatattctac agtttcaatt ccctaacaaa cagaggtata aaattgttgg    3480
gagtattcct taccatttaa gcacacaaat tattaaaaaa gtggtttttg aaagccatgc    3540
gtctgacatc tatctgattg ttgaagaagg attctacaag cgtaccttgg atattcaccg    3600
aacactaggg ttgctcttgc acactcaagt ctcgattcag caattgctta agctgccagc    3660
```

```
ggaatgcttt catcctaaac caaaagtaaa cagtgtctta ataaaactta cccgccatac    3720
cacagatgtt ccagataaat attggaagct atatacgtac tttgtttcaa aatgggtcaa    3780
tcgagaatat cgtcaactgt ttactaaaaa tcagtttcat caagcaatga aacacgccaa    3840
agtaaacaat ttaagtaccg ttacttatga gcaagtattg tctatttta atagttatct    3900 attatttaac gggaggaaat aattctatga gtcgcttttg taaatttgga aagttacacg    3960
ttactaaagg gaatgtagat aaattattag gtatactact gacagcttcc aagcatatgg    4020
cggccgcctg cagctggcgc catcgatacg cgtacgtcgc gaccgcggac atgtacagag    4080
ctcgagaagt actagtggcc acgtgggccg tgcaccttaa gcttggcgta atcatggtca    4140
tagctgtttc ctgtgtgaaa ttgttatccg ctcacaattc cacacaacat acgagccgga    4200
agcataaagt gtaaagcctg gggtgcctaa tgagtgagct aactcacatt aattgcgttg    4260
cgctcactgc ccgctttcca gtcgggaaac ctgtcgtgcc agctgcatta atgaatcggc    4320
caacgcgcgg ggagaggcgg tttgcgtatt gggcgc                              4356

<210> SEQ ID NO 10
<211> LENGTH: 25
<212> TYPE: DNA
<213> ORGANISM: Artificial Sequence
<220> FEATURE:
<223> OTHER INFORMATION: Forward primer pGT232 amplification reaction.

<400> SEQUENCE: 10
tagctgagtc gacaacagtt gttaa                                          25

<210> SEQ ID NO 11
<211> LENGTH: 30
<212> TYPE: DNA
<213> ORGANISM: Artificial Sequence
<220> FEATURE:
<223> OTHER INFORMATION: Reverse primer pGT232 amplification reaction.

<400> SEQUENCE: 11
tctaagaaac catggaggat ttattctctc                                     30

<210> SEQ ID NO 12
<211> LENGTH: 3054
<212> TYPE: DNA
<213> ORGANISM: Artificial Sequence
<220> FEATURE:
<223> OTHER INFORMATION: Sequenced pGT232 inserted into pSLER1 for
      pSLERGT

<400> SEQUENCE: 12
ccatggagga tttattctct ccgcagtttt gagcttaatc gtctcattaa ctactgcact    60
tttctccgat tggcttcgtc ggagaaaata atctaacggc atgaagcgca aattaaaagc    120
cactcaacta tgggcctagt tgggtggctt ttttgcaacc attacggttt tacttctcta    180
taagaattat agcatcaatc ttcatcatta gccaactcaa tagaagctcg atatagatca    240
tgttgagctt tatccaagct atctaaaagt tcgccataaa tatcaatatt tttcttttca    300
gcaaccaatt ttttcaaatc ttgaagatta tcagcaatct gttctgccat aactccatag    360
atttcagctt gtttcttcat attgtcaatt gtcttaatat cttgtaactc cattcctatc    420
actcccatct tacatagtta cttaccttag aattccaacg atatatcaca gtatctacaa    480
catcatcttc ttcttttcg tcatccacat taattagatc atcttctttt tcgtccagca    540
ataactcatg atgaatctct tttagtaatc ccgcaaagct taattgtcga gttccagcca    600
```

```
gagcatgctc gagctcgtca acaacaacta aatcgccttt ctcatcatcc gtaatataat    660
cataatcttt aacttgatat ttacttactt cttttgccga agcaatcaaa ctattatctt    720
tttttgacgc ccgaattttc ttgatattaa caatcggctt gtagtctaat ttccttgctc    780
gcttccataa ttgtgaccaa ttctcttggg taagataatg acccttagaa aaataactag    840
atttcaccat taacaaaata tgtacatgtt gatggaaagt tagactatct cgattgaccg    900
ttatttctgt agatcgcaca taaccaagaa gatcttttt tacatcttta tattgaaaaa    960
gccgataaat tgaacgattc atcgaagtaa gatttttct aagctcgccc aactttgagc   1020
tttcctcagt taatgtcaag aacagaaata tagcactagg atccttttta tatgctgtat   1080
ctaaaatttg acgcaactca taagaatttt tcatcgatcg gcgccagcta cataatggac   1140
aaagtctcga atgacaaaac cacgtttgat ataactttaa accattatca gttttcgcaa   1200
attgaagaac ttctccgcac tttgaaacgt tatgagcttt tttaaaattt aaaacctcca   1260
gatattggga ataagttaag ttagcaagtt ttttctgctt ccacggtcta actttcccat   1320
tactagaggt atcttttaga atttcttttt tatacatttc ttatacctct aactgcaaaa   1380
actacaagca gtcagagtta gttatcattg atatattcct aatgacatat tataataggg   1440
ttcgaagtta ataacgataa ctaactcatg catcgacggc caaatcgaac aactgcatga   1500
gttttttatt taattcttac aatgcttatt atacaccaaa aagtgttata ttttaaaatc   1560
ctaataaacc cagtcatatc aagggtttaa cccaatttca aaaaatggcg ttgtttctat   1620
atgtatcaag ataagaagaa actcgcttac agcgagtttc taaatagggg tttcacccct   1680
aaaaccctga ccagctgagc cagctggacc gcatttcccc tcgccgggcg ggcgtaaagc   1740
ggaaaaaatg acttttttct cgctttcgct caactagggt cttcccgtct caccatgtca   1800
agcgctgccc ttccgctacg ctccaggcgt tgtcgcttg acactcacct actaacagcg   1860
ggcttcgcca ccagtctact atctgcaaca cggcaacaag attaatcaga atatgcattg   1920
aagcagtgcg ctccgctcct tgtcttgcga caaagcgagc gcactgcttc aatgcttttt   1980
tattttctga attccataac tcgataatta gaaaagtta gtccgttaga aacgtctgcc   2040
acgccgagga agtcattcca gtttgaccac tcaaatcatc agcgacatca ttgagataat   2100
caatcagcaa ttttctagtt tctatctgct ttggaatttt taccacagcc aaaattgagt   2160
cccacttagc aatcacaaaa gattttctga cggctttatt agccttttcc gcactaatat   2220
ttttcgcttt atctcgttta ttttgatcgg tcgatggtat ccgatcgact gttgttacag   2280
catttgacgc aggttgctag ataaacgact agaccgaata atttttattc caactatttt   2340
tgcaaccaaa aaaatcacaa aataatcaac caataaaacg ataactaact tcttgctaca   2400
tccgattaat ttttctccag cctgccagaa atcggcccaa atattgaaat attgaggaaa   2460
ttttgggctg aaaaaaacat taatttttc ggcaaacaag ccaacacagc caagcagaaa   2520
agctaagaaa ataagttcca gccaattaaa aaatcgccac gaaagagaaa aaaatcggtc   2580
aaaataaatc gaacttgatt tcattttcta gcccccgaag tcttcgataa acggcgccat   2640
aaaaggaact acacggtttt ccggttgagt acttgcaagc cctaacccct tagaaaagcc   2700
gtcatgatta acaactgttg tcgactcagc tagggcccta tatatggatc caattgcaat   2760
gatcatcatg acagatctgc gcgcgatcga tatcagcgct ttaaatttgc gcatgctagc   2820
tatagttcta gaggtaccgg ttgttaacgt tagccggcta cgtatactcc ggaatattaa   2880
taggcctagg atgcatatgc ttagaagcaa acttaagagt gtgttgatag tgcagtatct   2940
taaaattttg tataatagga attgaagtta aattagatgc taaaaatttg taattaagaa   3000
```

```
ggagtgatta catgaacaaa aatataaaat attctcaaaa cttttttaacg agtg        3054
```

<210> SEQ ID NO 13
<211> LENGTH: 9013
<212> TYPE: DNA
<213> ORGANISM: Artificial Sequence
<220> FEATURE:
<223> OTHER INFORMATION: pHENOMM

<400> SEQUENCE: 13

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
ttttttccata ggctccgccc ccctgacgag catcacaaaa atcgacgctc aagtcagagg    240
tggcgaaacc cgacaggact ataaagatac caggcgtttc ccccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc ttttcaata ttattgaagc atttatcagg gttattgtct catgagcgga   1860
tacatatttg aatgtatta gaaaaataaa caaatagggg ttccgcgcac atttccccga   1920
aaagtgccac ctgacgtcta agaaaccatt attatcatga cattaaccta taaaaatagg   1980
```

```
cgtatcacga ggcccttteg tctcgcgcgt ttcggtgatg acggtgaaaa cctctgacac    2040
atgcagctcc cggagacggt cacagcttgt ctgtaagcgg atgccgggag cagacaagcc    2100
cgtcagggcg cgtcagcggg tgttggcggg tgtcggggct ggcttaacta tgcggcatca    2160
gagcagattg tactgagagt gcaccataaa attgtaaacg ttaatatttt gttaaaattc    2220
gcgttaaatt tttgttaaat cagctcattt tttaaccaat aggccgaaat cggcaaaatc    2280
ccttataaat caaagaata gcccgagata gggttgagtg ttgttccagt ttggaacaag    2340
agtccactat taaagaacgt ggactccaac gtcaaggggc gaaaaaccgt ctatcagggc    2400
gatggcccac tacgtgaacc atcacccaaa tcaagttttt tggggtcgag gtgccgtaaa    2460
gcactaaatc ggaaccctaa agggagcccc cgatttagag cttgacgggg aaagccggcg    2520
aacgtggcga gaaaggaagg gaagaaagcg aaaggagcgg cgctagggc gctggcaagt     2580 gtagcggtca cgctgcgcgt aaccaccaca cccgccgcgc ttaatgcgcc gctacagggc    2640
gcgtactatg gttgctttga cgtatgcggt gtgaaatacc gcacagatgc gtaaggagaa    2700
aataccgcat caggcgccat cgccattca ggctgcgcaa ctgttgggaa gggcgatcgg    2760
tgcgggcctc ttcgctatta cgccagctgg cgaaaggggg atgtgctgca aggcgattaa    2820
gttgggtaac gccagggttt tcccagtcac gacgttgtaa aacgacggcc agtgaattcg    2880
aatggccatg gaggatttat tctctccgca gttttgagct taatcgtctc attaactact    2940
gcactttcct ccgattggct tcgtcggaga aaataatcta acggcatgaa gcgcaaatta    3000
aaagccactc aactatgggc ctagttgggt ggcttttttg caaccattac ggttttactt    3060
ctctataaga attatagcat caatcttcat cattagccaa ctcaatagaa gctcgatata    3120
gatcatgttg agcttatcc aagctatcta aaagttcgcc ataaatatca atattttct     3180 tttcagcaac caatttttc aaatcttgaa gattatcagc aatctgttct gccataactc    3240
catagatttc agcttgtttc ttcatattgt caattgtctt aatatcttgt aactccattc    3300
ctatcactcc catcttacat agttacttac cttagaattc caacgatata tcacagtatc    3360
tacaacatca tcttttcttt tttcgtcatc cacattaatt agatcatctt cttttcgtc    3420 cagcaataac tcatgatgaa tctcttttag taatcccgca aagcttaatt gtcgagttcc    3480
agccagagca tgctcgagct cgtcaacaac aactaaatcg cctttctcat catccgtaat    3540
ataatcataa tctttaactt gatatttact tacttctttt gccgaagcaa tcaaactatt    3600
atcttttttt gacgcccgaa ttttcttgat attaacaatc ggcttgtagt ctaatttcct    3660
tgctcgcttc cataattgtg accaattctc ttgggtaaga taatgaccct tagaaaaata    3720
actagatttc accattaaca aaatatgtac atgttgatgg aaagttagac tatctcgatt    3780
gaccgttatt tctgtagatc gcacataacc aagaagatct ttttttacat ctttatattg    3840
aaaaagccga taaattgaac gattcatcga agtaagattt tttctaagct cgcccaactt    3900 tgagcttttcc tcagttaatg tcaagaacag aaatatagca ctaggatcct ttttatatgc    3960
tgtatctaaa atttgacgca actcataaga atttttcatc gatcggcgcc agctacataa    4020
tggacaaagt ctcgaatgac aaaaccacgt ttgatataac tttaaaccat tatcagtttt    4080
cgcaaattga agaacttctc cgcactttga aacgttatga gcttttttaa aatttaaaac    4140
ctccagatat tgggaataag ttaagttagc aagttttttc tgcttccacg gtctaacttt    4200
cccattacta gaggtatctt ttagaatttc ttttttatac attttcttata cctctaactg    4260 caaaaactac aagcagtcag agttagttat cattgatata ttcctaatga catattataa    4320
tagggttcga agttaataac gataactaac tcatgcatcg acggccaaat cgaacaactg    4380
```

```
catgagtttt ttatttaatt cttacaatgc ttattataca ccaaaaagtg ttatatttta    4440
aaatcctaat aaacccagtc atatcaaggg tttaacccaa tttcaaaaaa tggcgttgtt    4500
tctatatgta tcaagataag aagaaactcg cttacagcga gtttctaaat aggggtttca    4560
cccctaaaac cctgaccagc tgagccagct ggaccgcatt tccctcgcc gggcgggcgt     4620 aaagcggaaa aaatgacttt tttctcgctt tcgctcaact agggtcttcc cgtctcacca    4680
tgtcaagcgc tgcccttccg ctacgctcca ggcgtttgtc gcttgacact cacctactaa    4740
cagcgggctt cgccaccagt ctactatctg caacacggca acaagattaa tcagaatatg    4800
cattgaagca gtgcgctccg ctccttgtct tgcgacaaag cgagcgcact gcttcaatgc    4860 tttttttattt tctgaattcc ataactcgat aattagaaaa agttagtccg ttagaaacgt    4920
ctgccacgcc gaggaagtca ttccagtttg accactcaaa tcatcagcga catcattgag    4980
ataatcaatc agcaatttc tagtttctat ctgctttgga attttacca cagccaaaat     5040 tgagtcccac ttagcaatca caaaagattt tctgacggct ttattagcct tttccgcact    5100 aatattttc gctttatctc gtttattttg atcggtcgat ggtatccgat cgactgttgt     5160
tacagcattt gacgcaggtt gctagataaa cgactagacc gaataatttt tattccaact    5220 attttttgcaa ccaaaaaaat cacaaaataa tcaaccaata aaacgataac taacttcttg    5280
ctacatccga ttaattttc tccagcctgc cagaaatcgg cccaaatatt gaaatattga     5340
ggaaattttg ggctgaaaaa aacattaatt ttttcggcaa acaagccaac acagccaagc    5400
agaaaagcta agaaaataag ttccagccaa ttaaaaaatc gccacgaaag agaaaaaaat    5460
cggtcaaaat aaatcgaact tgatttcatt ttctagcccc cgaagtcttc gataaacggc    5520
gccataaaag gaactacacg gttttccggt tgagtacttg caagccctaa ccccttagaa    5580
aagccgtcat gattaacaac tgttgtcgac ttttttttga taagttaagg gatgcagttt    5640 atgcaccct taacttatca ttattagtgt aaacaaggaa ggatatcttg tacggcttga     5700
acaattacac caccagcagc gatatcagca gaaatacgag caatatgttc gtcaagtcct    5760
tgttcgttat cgttccaaat atatggccga tctgatgtag gttttttggcc gacaacatga    5820 cgtactgctg aataaagacg ttctgtagct ggacttaaac aagcacgagc atcataatgg    5880
cccgtctttt tgtaagtccg taaatcaaca gcttgtactc caaacattaa tgcaatagct    5940
acgtagtttt gaaaaatatc aacagaccgt cgtgctaacg tagcagaagt gtatccttga    6000
gagttaatat tttggttaaa ttgttcggcg tgtgtaggaa agcgatcagc aattgaattt    6060
ccgtaaaaag tcaacaatgg cataattgag ttgccacaaa tttgcaaacc cttaagaccc    6120
atgtttacct ttcgttcccg gtttcccaat aatgatggtg gaagtccgtt actgaattct    6180
ggactggcca aaagtgcaat ttggacatcc aaatgctttg caagaagacc aatgtagtaa    6240
cgtaagtggt ccatgcccat gccaacatat tgacccaaaa agttaccgcc atggtatgag    6300
gcttggttat caacgtcaat taatggattg tcagtgacac tattaatttc gatttcaatt    6360
tgcttagcaa tttgtgaaat tccatcaaca ataggaccca aatattgtgg taagcaacgt    6420
aaactatagc ggtcttgaat aagttcatga tcacgataat catgcttacc atctaattcg    6480
tcgcgaacaa gttgactatt agctaaaaga gaaatcattt gatcagcagc ccaaagttga    6540
cctgggtgag gtttagaatt gtgaatgaat gggtggaaac tttgatttgt gccattaagt    6600
gcttgaatat ctaaggcatg aacacccatg gcaatagcag taagaatttg agtatcataa    6660
acgcaattag cagcaattcc cgtcataact gatgtaccat tcatcatagc aagaccttct    6720
```

```
tttggaagta atgtaagtgg tgataaattt aattgtcgaa gagctgttgg ggcatccatt    6780
tctttaccat taaaatcaac tttgaatgat ggatccaaac caattaaaga acctgtaata    6840
taagataaag gaacaagatc tccacttgca ccaattgatc cgaattcgta aacataaggt    6900
gtaacaccgg cgttaaggaa aatttccata cgcttaatta attcaagacg aataccagaa    6960
gcgccacgca tgtgtgaatt tgcacgtaat aacatagcag cacgaacatc tgctaatgga    7020
agtttattac cagctcctgt tttaagaaac caaacaagat tagtttgaag ttcagaagct    7080
tgttcacgac taatagcgac gtttgccatt ccaccgaatc ctgaagtaac accataaatt    7140
ggttctcctg attcaacagc gttattgata tagtcgcaac tagcttgaat gccttgtaaa    7200
atgtcagtgt tgttagttaa actaactaaa gtaccattgc gtgcaacccg tgcaacatcg    7260
ttaatagtaa gcttttgatt accaatgata acattagcac ttgagtttcc agtaaatgag    7320
aattgttgag aactagtctt agattgtgct tgagataaag tcttcattta tacctactcc    7380
ttcttaatta caaattttta gcatctaatt taacttcaat tcctattata caaaatttta    7440
agatactgca ctatcaacac actcttgaac atatgcatcc taggtcgtct attaatactt    7500
ccaggagtat acgtagccag gctaacgtta atcaaccagg tatcctctag aactatagct    7560
agcatgccta tatggatc caattgcaat gatcatcatg acagatctgc gcgcgatcga    7620
tatcagcgct ttaaatttgc gcatgctagc tatagttcta gaggtaccgg ttgttaacgt    7680
tagccggcta cgtatactcc ggaatattaa taggcctagg atgcatatgc ttagaagcaa    7740
acttaagagt gtgttgatag tgcagtatct taaaattttg tataatagga attgaagtta    7800
aattagatgc taaaaatttg taattaagaa ggagtgatta catgaacaaa aatataaaat    7860
attctcaaaa cttttttaacg agtgaaaaag tactcaacca aataataaaa caattgaatt    7920
taaaagaaac cgataccgtt tacgaaattg aacaggtaa aagggcattta acgacgaaac    7980
tggctaaaat aagtaaacag gtaacgtcta ttgaattaga cagtcatcta ttcaacttat    8040
cgtcagaaaa attaaaactg aatactcgtg tcactttaat tcaccaagat attctacagt    8100
ttcaattccc taacaaacag aggtataaaa ttgttgggag tattccttac catttaagca    8160
cacaaattat taaaaaagtg gttttttgaaa gccatgcgtc tgacatctat ctgattgttg    8220
aagaaggatt ctacaagcgt accttggata ttcaccgaac actagggttg ctcttgcaca    8280
ctcaagtctc gattcagcaa ttgcttaagc tgccagcgga atgctttcat cctaaaccaa    8340
aagtaaacag tgtcttaata aaacttaccc gccataccac agatgttcca gataaatatt    8400
ggaagctata tacgtacttt gtttcaaaat gggtcaatcg agaatatcgt caactgttta    8460
ctaaaaatca gtttcatcaa gcaatgaaac acgccaaagt aaacaattta agtaccgtta    8520
cttatgagca agtattgtct attttttaata gttatctatt atttaacggg aggaaataat    8580
tctatgagtc gcttttgtaa atttggaaag ttacacgtta ctaaagggaa tgtagataaa    8640
ttattaggta tactactgac agcttccaag catatggcgg ccgcctgcag ctggcgccat    8700
cgatacgcgt acgtcgcgac cgcggacatg tacagagctc gagaagtact agtggccacg    8760
tgggccgtgc accttaagct tggcgtaatc atggtcatag ctgtttcctg tgtgaaattg    8820
ttatccgctc acaattccac acaacatacg agccggaagc ataaagtgta aagcctgggg    8880
tgcctaatga gtgagctaac tcacattaat tgcgttgcgc tcactgcccg ctttccagtc    8940
gggaaacctg tcgtgccagc tgcattaatg aatcggccaa cgcgcgggga gaggcggttt    9000
gcgtattggg cgc                                                      9013
```

<210> SEQ ID NO 14
<211> LENGTH: 9142
<212> TYPE: DNA
<213> ORGANISM: Artificial Sequence
<220> FEATURE:
<223> OTHER INFORMATION: pHENOMM-sec

<400> SEQUENCE: 14

```
tcttccgctt cctcgctcac tgactcgctg cgctcggtcg ttcggctgcg gcgagcggta      60
tcagctcact caaaggcggt aatacggtta tccacagaat cagggataa cgcaggaaag     120 aacatgtgag caaaaggcca gcaaaaggcc aggaaccgta aaaaggccgc gttgctggcg     180
tttttccata ggctccgccc ccctgacgag catcacaaaa atcgacgctc aagtcagagg     240
tggcgaaacc cgacaggact ataaagatac caggcgtttc ccctggaag ctccctcgtg     300 cgctctcctg ttccgaccct gccgcttacc ggatacctgt ccgcctttct ccttcggga     360 agcgtggcgc tttctcatag ctcacgctgt aggtatctca gttcggtgta ggtcgttcgc     420
tccaagctgg gctgtgtgca cgaaccccc gttcagcccg accgctgcgc cttatccggt     480
aactatcgtc ttgagtccaa cccggtaaga cacgacttat cgccactggc agcagccact     540
ggtaacagga ttagcagagc gaggtatgta ggcggtgcta cagagttctt gaagtggtgg     600
cctaactacg gctacactag aagaacagta tttggtatct gcgctctgct gaagccagtt     660
accttcggaa aaagagttgg tagctcttga tccggcaaac aaaccaccgc tggtagcggt     720 ggttttttg tttgcaagca gcagattacg cgcagaaaaa aaggatctca agaagatcct     780
ttgatctttt ctacggggtc tgacgctcag tggaacgaaa actcacgtta agggattttg     840
gtcatgagat tatcaaaaag gatcttcacc tagatccttt taaattaaaa atgaagtttt     900
aaatcaatct aaagtatata tgagtaaact tggtctgaca gttaccaatg cttaatcagt     960
gaggcaccta tctcagcgat ctgtctattt cgttcatcca tagttgcctg actccccgtc    1020
gtgtagataa ctacgatacg ggagggctta ccatctggcc ccagtgctgc aatgataccg    1080
cgagacccac gctcaccggc tccagattta tcagcaataa accagccagc cggaagggcc    1140
gagcgcagaa gtggtcctgc aactttatcc gcctccatcc agtctattaa ttgttgccgg    1200
gaagctagag taagtagttc gccagttaat agtttgcgca acgttgttgc cattgctaca    1260
ggcatcgtgg tgtcacgctc gtcgtttggt atggcttcat tcagctccgg ttcccaacga    1320
tcaaggcgag ttacatgatc ccccatgttg tgcaaaaaag cggttagctc cttcggtcct    1380
ccgatcgttg tcagaagtaa gttggccgca gtgttatcac tcatggttat ggcagcactg    1440
cataattctc ttactgtcat gccatccgta agatgctttt ctgtgactgg tgagtactca    1500
accaagtcat tctgagaata gtgtatgcgg cgaccgagtt gctcttgccc ggcgtcaata    1560
cgggataata ccgcgccaca tagcagaact ttaaaagtgc tcatcattgg aaaacgttct    1620
tcggggcgaa aactctcaag gatcttaccg ctgttgagat ccagttcgat gtaacccact    1680
cgtgcaccca actgatcttc agcatctttt actttcacca cgtttctgg gtgagcaaaa    1740 acaggaaggc aaaatgccgc aaaaaaggga ataagggcga cacggaaatg ttgaatactc    1800
atactcttcc ttttcaata ttattgaagc atttatcagg gttattgtct catgagcgga    1860
tacatatttg aatgtattta gaaaaataaa caaataggg ttccgcgcac atttccccga    1920
aaagtgccac ctgacgtcta agaaaccatt attatcatga cattaaccta taaaaatagg    1980
cgtatcacga ggccctttcg tctcgcgcgt ttcggtgatg acggtgaaaa cctctgacac    2040
atgcagctcc cggagacggt cacagcttgt ctgtaagcgg atgccgggag cagacaagcc    2100
```

```
cgtcagggcg cgtcagcggg tgttggcggg tgtcggggct ggcttaacta tgcggcatca    2160
gagcagattg tactgagagt gcaccataaa attgtaaacg ttaatatttt gttaaaattc    2220
gcgttaaatt tttgttaaat cagctcattt tttaaccaat aggccgaaat cggcaaaatc    2280
ccttataaat caaagaaata gcccgagata gggttgagtg ttgttccagt ttggaacaag    2340
agtccactat taaagaacgt ggactccaac gtcaaagggc gaaaaaccgt ctatcagggc    2400
gatggcccac tacgtgaacc atcacccaaa tcaagttttt tggggtcgag gtgccgtaaa    2460
gcactaaatc ggaaccctaa agggagcccc cgatttagag cttgacgggg aaagccggcg    2520
aacgtggcga aaggaagg gaagaaagcg aaaggagcgg cgctagggc gctggcaagt    2580 gtagcggtca cgctgcgcgt aaccaccaca cccgccgcgc ttaatgcgcc gctacagggc    2640
gcgtactatg gttgctttga cgtatgcggt gtgaaatacc gcacagatgc gtaaggagaa    2700
aataccgcat caggcgccat cgccattca ggctgcgcaa ctgttgggaa gggcgatcgg    2760
tgcgggcctc ttcgctatta cgccagctgg cgaaagggg atgtgctgca aggcgattaa    2820
gttgggtaac gccagggttt tcccagtcac gacgttgtaa aacgacggcc agtgaattcg    2880
aatggccatg gaggatttat tctctccgca gttttgagct taatcgtctc attaactact    2940 gcactttct ccgattggct tcgtcggaga aaataatcta acggcatgaa gcgcaaatta    3000
aaagccactc aactatgggc ctagttgggt ggcttttttg caaccattac ggttttactt    3060
ctctataaga attatagcat caatcttcat cattagccaa ctcaatagaa gctcgatata    3120
gatcatgttg agctttatcc aagctatcta aaagttcgcc ataaatatca atattttct    3180 tttcagcaac caattttttc aaatcttgaa gattatcagc aatctgttct gccataactc    3240
catagatttc agcttgtttc ttcatattgt caattgtctt aatatcttgt aactccattc    3300
ctatcactcc catcttacat agttacttac cttagaattc caacgatata tcacagtatc    3360
tacaacatca tcttttcctt tttcgtcatc cacattaatt agatcatctt cttttttcgtc    3420 cagcaataac tcatgatgaa tctcttttag taatcccgca aagcttaatt gtcgagttcc    3480
agccagagca tgctcgagct cgtcaacaac aactaaatcg cctttctcat catccgtaat    3540
ataatcataa tctttaactt gatatttact tacttctttt gccgaagcaa tcaaactatt    3600
atcttttttt gacgcccgaa ttttcttgat attaacaatc ggcttgtagt ctaatttcct    3660
tgctcgcttc cataattgtg accaattctc ttgggtaaga taatgaccct tagaaaaata    3720
actagatttc accattaaca aaatatgtac atgttgatgg aaagttagac tatctcgatt    3780
gaccgttatt tctgtagatc gcacataacc aagaagatct tttttacat ctttatattg    3840 aaaaagccga taattgaac gattcatcga agtaagattt tttctaagct cgcccaactt    3900 tgagcttttcc tcagttaatg tcaagaacag aaatatagca ctaggatcct ttttatatgc    3960
tgtatctaaa atttgacgca actcataaga atttttcatc gatcggcgcc agctacataa    4020
tggacaaagt ctcgaatgac aaaaccacgt ttgatataac tttaaaccat tatcagtttt    4080
cgcaaattga agaacttctc cgcactttga aacgttatga gcttttttaa aatttaaaac    4140
ctccagatat tgggaataag ttaagttagc aagttttttc tgcttccacg gtctaacttt    4200
cccattacta gaggtatctt ttagaatttc ttttttatac atttcttata cctctaactg    4260
caaaaactac aagcagtcag agttagttat cattgatata ttcctaatga catattataa    4320
tagggttcga agttaataac gataactaac tcatgcatcg acggccaaat cgaacaactg    4380
catgagtttt ttatttaatt cttacaatgc ttattataca ccaaaaagtg ttatatttta    4440
aaatcctaat aaacccagtc atatcaaggg tttaacccaa tttcaaaaaa tggcgttgtt    4500
```

```
tctatatgta tcaagataag aagaaactcg cttacagcga gtttctaaat aggggtttca    4560
cccctaaaac cctgaccagc tgagccagct ggaccgcatt tccccctcgcc gggcgggcgt    4620 aaagcggaaa aaatgacttt tttctcgctt tcgctcaact agggtcttcc cgtctcacca    4680
tgtcaagcgc tgcccttccg ctacgctcca ggcgtttgtc gcttgacact cacctactaa    4740
cagcgggctt cgccaccagt ctactatctg caacacggca acaagattaa tcagaatatg    4800
cattgaagca gtgcgctccg ctccttgtct tgcgacaaag cgagcgcact gcttcaatgc    4860
ttttttattt tctgaattcc ataactcgat aattagaaaa agttagtccg ttagaaacgt    4920
ctgccacgcc gaggaagtca ttccagtttg accactcaaa tcatcagcga catcattgag    4980
ataatcaatc agcaattttc tagtttctat ctgctttgga attttttacca cagccaaaat    5040 tgagtcccac ttagcaatca caaaagattt tctgacggct ttattagcct tttccgcact    5100 aatattttc  gctttatctc gtttattttg atcggtcgat ggtatccgat cgactgttgt    5160
tacagcattt gacgcaggtt gctagataaa cgactagacc gaataatttt tattccaact    5220 attttttgcaa ccaaaaaaat cacaaaataa tcaaccaata aaacgataac taacttcttg    5280
ctacatccga ttaattttc  tccagcctgc cagaaatcgg cccaaatatt gaaatattga    5340
ggaaattttg ggctgaaaaa aacattaatt ttttcggcaa acaagccaac acagccaagc    5400
agaaaagcta agaaaataag ttccagccaa ttaaaaaatc gccacgaaag agaaaaaaat    5460
cggtcaaaat aaatcgaact tgatttcatt ttctagcccc cgaagtcttc gataaacggc    5520
gccataaaag gaactacacg gttttccggt tgagtacttg caagccctaa ccccttagaa    5580
aagccgtcat gattaacaac tgttgtcgac ttttttttga taagttaagg gatgcagttt    5640 atgcaccct  taacttatca ttattagtgt aaacaaggaa ggatatcttg tacggcttga    5700
acaattacac caccagcagc gatatcagca gaaatacgag caatatgttc gtcaagtcct    5760
tgttcgttat cgttccaaat atatggccga tctgatgtag gttttttggcc gacaacatga    5820 cgtactgctg aataaagacg ttctgtagct ggacttaaac aagcacgagc atcataatgg    5880
cccgtctttt tgtaagtccg taaatcaaca gcttgtactc caaacattaa tgcaatagct    5940
acgtagtttt gaaaaatatc aacagaccgt cgtgctaacg tagcagaagt gtatccttga    6000
gagttaatat tttggttaaa ttgttcggcg tgtgtaggaa agcgatcagc aattgaattt    6060
ccgtaaaaag tcaacaatgg cataattgag ttgccacaaa tttgcaaacc cttaagaccc    6120
atgtttacct ttcgttcccg gtttcccaat aatgatggtg gaagtccgtt actgaattct    6180
ggactggcca aaagtgcaat ttggacatcc aaatgctttg caagaagacc aatgtagtaa    6240
cgtaagtggt ccatgcccat gccaacatat tgacccaaaa agttaccgcc atggtatgag    6300
gcttggttat caacgtcaat taatggattg tcagtgacac tattaatttc gatttcaatt    6360
tgcttagcaa tttgtgaaat tccatcaaca ataggaccca aatattgtgg taagcaacgt    6420
aaactatagc ggtcttgaat aagttcatga tcacgataat catgcttacc atctaattcg    6480
tcgcgaacaa gttgactatt agctaaaaga gaaatcattt gatcagcagc ccaaagttga    6540
cctgggtgag gttagaatt gtgaatgaat gggtggaaac tttgatttgt gccattaagt    6600
gcttgaatat ctaaggcatg aacacccatg gcaaatagcag taagaatttg agtatcataa    6660
acgcaattag cagcaattcc cgtcataact gatgtaccat tcatcatagc aagaccttct    6720
tttggaagta atgtaagtgg tgataaattt aattgtcgaa gagctgttgg ggcatccatt    6780
tctttaccat taaaatcaac tttgaatgat ggatccaaac caattaaaga acctgtaata    6840
```

```
taagataaag gaacaagatc tccacttgca ccaattgatc cgaattcgta aacataaggt   6900
gtaacaccgg cgttaaggaa aatttccata cgcttaatta attcaagacg aataccagaa   6960
gcgccacgca tgtgtgaatt tgcacgtaat aacatagcag cacgaacatc tgctaatgga   7020
agtttattac cagctcctgt tttaagaaac caaacaagat tagtttgaag ttcagaagct   7080
tgttcacgac taatagcgac gtttgccatt ccaccgaatc ctgaagtaac accataaatt   7140
ggttctcctg attcaacagc gttattgata tagtcgcaac tagcttgaat gccttgtaaa   7200
atgtcagtgt tgttagttaa actaactaaa gtaccattgc gtgcaacccg tgcaacatcg   7260
ttaatagtaa gcttttgatt accaatgata acattagcac ttgagtttcc agtaaatgag   7320
aattgttgag aactagtctt agattgtgct tgagataaag tcttcattta tacctactcc   7380
tatcaactga agaagcatca acaaccataa tattttggct tacgcccaa  aaactaataa   7440
cgaccaataa tggtaatagc cacacaggaa gtccgttacg gtgatgttta cctgtatttt   7500
cagtatacat tcttaattac aaattttag catctaattt aacttcaatt cctattatac   7560
aaaattttaa gatactgcac tatcaacaca ctcttgaaca tatgcatcct aggtcgtcta   7620
ttaatacttc caggagtata cgtagccagg ctaacgttaa tcaaccaggt atcctctaga   7680
actatagcta gcatgcctat atatggatcc aattgcaatg atcatcatga cagatctgcg   7740
cgcgatcgat atcagcgctt taaatttgcg catgctagct atagttctag aggtaccggt   7800
tgttaacgtt agccggctac gtatactccg gaatattaat aggcctagga tgcatatgct   7860
tagaagcaaa cttaagagtg tgttgatagt gcagtatctt aaaatttgt  ataataggaa   7920
ttgaagttaa attagatgct aaaaatttgt aattaagaag gagtgattac atgaacaaaa   7980
atataaaata ttctcaaaac tttttaacga gtgaaaaagt actcaaccaa ataataaaac   8040
aattgaattt aaaagaaacc gataccgttt acgaaattgg aacaggtaaa gggcatttaa   8100
cgacgaaact ggctaaaata agtaaacagg taacgtctat tgaattagac agtcatctat   8160
tcaacttatc gtcagaaaaa ttaaaactga atactcgtgt cactttaatt caccaagata   8220
ttctacagtt tcaattccct aacaaacaga ggtataaaat tgttgggagt attccttacc   8280
atttaagcac acaaattatt aaaaaagtgg ttttttgaaag ccatgcgtct gacatctatc   8340
tgattgttga agaaggattc tacaagcgta ccttggatat tcaccgaaca ctagggttgc   8400
tcttgcacac tcaagtctcg attcagcaat tgcttaagct gccagcggaa tgctttcatc   8460
ctaaaccaaa agtaaacagt gtcttaataa aacttacccg ccataccaca gatgttccag   8520
ataaatattg gaagctatat acgtactttg tttcaaaatg ggtcaatcga gaatatcgtc   8580
aactgtttac taaaaatcag tttcatcaag caatgaaaca cgccaaagta aacaatttaa   8640
gtaccgttac ttatgagcaa gtattgtcta tttttaatag ttatctatta tttaacggga   8700
ggaaataatt ctatgagtcg cttttgtaaa tttggaaagt tacacgttac taagggaat   8760
gtagataaat tattaggtat actactgaca gcttccaagc atatggcggc cgcctgcagc   8820
tggcgccatc gatacgcgta cgtcgcgacc gcggacatgt acagagctcg agaagtacta   8880
gtggccacgt gggccgtgca ccttaagctt ggcgtaatca tggtcatagc tgtttcctgt   8940
gtgaaattgt tatccgctca caattccaca acaacatacga gccggaagca taagtgtaa   9000
agcctggggt gcctaatgag tgagctaact cacattaatt gcgttgcgct cactgcccgc   9060
tttccagtcg ggaaacctgt cgtgccagct gcattaatga atcggccaac gcgcggggag   9120
aggcggtttg cgtattgggc gc                                            9142
```

```
<210> SEQ ID NO 15
<211> LENGTH: 1963
<212> TYPE: DNA
<213> ORGANISM: Artificial Sequence
<220> FEATURE:
<223> OTHER INFORMATION: synthesized

<400> SEQUENCE: 15
gcatgctagc tatagttcta gaggatacct ggttgattaa cgttagcctg gctacgtata      60
ctcctggaag tattaataga cgacctagga tgcatatgtt caagagtgtg ttgatagtgc     120
agtatcttaa aattttgtat aataggaatt gaagttaaat tagatgctaa aaatttgtaa     180
ttaagaagga gtaggtataa atgaagactt tatctcaagc acaatctaag actagttctc     240
aacaattctc atttactgga aactcaagtg ctaatgttat cattggtaat caaaagctta     300
ctattaacga tgttgcacgg gttgcacgca atggtacttt agttagttta actaacaaca     360
ctgacatttt acaaggcatt caagctagtt gcgactatat caataacgct gttgaatcag     420
gagaaccaat ttatggtgtt acttcaggat tcggtggaat ggcaaacgtc gctattagtc     480
gtgaacaagc ttctgaactt caaactaatc ttgtttggtt tcttaaaaca ggagctggta     540
ataaacttcc attagcagat gttcgtgctg ctatgttatt acgtgcaaat tcacacatgc     600
gtggcgcttc tggtattcgt cttgaattaa ttaagcgtat ggaaattttc cttaacgccg     660
gtgttacacc ttatgtttac gaattcggat caattggtgc aagtggagat cttgttcctt     720
tatcttatat tacaggttct ttaattggtt tggatccatc attcaaagtt gattttaatg     780
gtaaagaaat ggatgcccca acagctcttc gacaattaaa tttatcacca cttacattac     840
ttccaaaaga aggtcttgct atgatgaatg gtacatcagt tatgacggga attgctgcta     900
attgcgttta tgatactcaa attcttactg ctattgccat gggtgttcat gccttagata     960
ttcaagcact taatggcaca aatcaaagtt ccacccatt cattcacaat tctaaacctc    1020
acccaggtca actttgggct gctgatcaaa tgatttctct tttagctaat agtcaacttg    1080
ttcgcgacga attagatggt aagcatgatt atcgtgatca tgaacttatt caagaccgct    1140
atagtttacg ttgcttacca caatatttgg gtcctattgt tgatggaatt tcacaaattg    1200
ctaagcaaat tgaaatcgaa attaatagtg tcactgacaa tccattaatt gacgttgata    1260
accaagcctc ataccatggc ggtaactttt tgggtcaata tgttggcatg gcatggacc     1320 acttacgtta ctacattggt cttcttgcaa agcatttgga tgtccaaatt gcacttttgg    1380
ccagtccaga attcagtaac ggacttccac catcattatt gggaaaccgg gaacgaaagg    1440
taaacatggg tcttaagggt ttgcaaattt gtggcaactc aattatgcca ttgttgactt    1500
tttacggaaa ttcaattgct gatcgctttc ctacacacgc cgaacaattt aaccaaaata    1560
ttaactctca aggatacact tctgctacgt tagcacgacg gtctgttgat attttcaaa     1620 actacgtagc tattgcatta atgtttggag tacaagctgt tgatttacgg acttacaaaa    1680
agacgggcca ttatgatgct cgtgcttgtt taagtccagc tacagaacgt ctttattcag    1740
cagtacgtca tgttgtcggc caaaaaccta catcagatcg gccatatatt tggaacgata    1800
acgaacaagg acttgacgaa catattgctc gtatttctgc tgatatcgct gctggtggtg    1860
taattgttca agccgtacaa gatatccttc cttgtttaca ctaataatga taagttaagg    1920
ggtgcataaa ctgcatccct taacttatca aaaaaagtc gac                      1963
```